US012472357B2

(12) United States Patent
Dieken et al.

(10) Patent No.: US 12,472,357 B2
(45) Date of Patent: Nov. 18, 2025

(54) MULTIPLE TYPE SLEEP APNEA

(71) Applicant: INSPIRE MEDICAL SYSTEMS, INC., Golden Valley, MN (US)

(72) Inventors: David Dieken, Golden Valley, MN (US); Kevin Verzal, Golden Valley, MN (US); John Rondoni, Golden Valley, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 610 days.

(21) Appl. No.: 16/681,156

(22) Filed: Nov. 12, 2019

(65) Prior Publication Data

US 2020/0147376 A1 May 14, 2020

Related U.S. Application Data

(60) Provisional application No. 62/760,097, filed on Nov. 13, 2018.

(51) Int. Cl.

| | |
|---|---|
| ***A61N 1/00*** | (2006.01) |
| ***A61N 1/36*** | (2006.01) |
| ***A61N 1/378*** | (2006.01) |

(52) U.S. Cl.
CPC ........ *A61N 1/3611* (2013.01); *A61N 1/36139* (2013.01); *A61N 1/378* (2013.01)

(58) Field of Classification Search
CPC ... A61N 1/3611; A61N 1/36139; A61N 1/378
USPC .......................................................... 607/42
See application file for complete search history.

(56) References Cited

U.S. PATENT DOCUMENTS

| | | | |
|---|---|---|---|
| 5,146,918 | A | 9/1992 | Kollok et al. |
| 6,463,327 | B1 | 10/2002 | Lurie et al. |
| 6,928,324 | B2 | 8/2005 | Park et al. |
| 7,155,278 | B2 | 12/2006 | King et al. |
| 7,225,021 | B1 | 5/2007 | Park et al. |
| 7,340,302 | B1 | 3/2008 | Falkenberg et al. |
| 7,371,220 | B1 | 5/2008 | Koh et al. |
| 7,510,531 | B2 | 3/2009 | Lee et al. |
| 7,678,058 | B2 | 3/2010 | Patangay et al. |

(Continued)

FOREIGN PATENT DOCUMENTS

| | | |
|---|---|---|
| WO | 2016069689 | 5/2016 |

OTHER PUBLICATIONS

International Search Report and the Written Opinion of the International Searching Authority, PCT/US2019/060917, Apr. 24, 2020, 18 pages.

*Primary Examiner* — Niketa Patel
*Assistant Examiner* — Anant A Gupta
(74) *Attorney, Agent, or Firm* — Dicke, Billig & Czaja, PLLC

(57) ABSTRACT

A method includes delivering, via a first stimulation element and during a treatment period, stimulation to an upper airway patency-related nerve to cause contraction of upper airway patency-related muscles. The method also may include delivering upon detecting central sleep apnea behavior, via a second stimulation element and during a treatment period, stimulation to a central sleep apnea-related nerve. The method also may include delivering the stimulation to the upper airway patency-related nerve independently of a decisional process and trigger to deliver stimulation to the different central sleep apnea-related nerve.

20 Claims, 19 Drawing Sheets

(56) References Cited

U.S. PATENT DOCUMENTS

| | | | | |
|---|---|---|---|---|
| 7,970,475 | B2 | 6/2011 | Tehrani et al. | |
| 7,976,470 | B2 | 7/2011 | Patangay et al. | |
| 8,160,711 | B2 | 4/2012 | Tehrani et al. | |
| 8,200,336 | B2 | 6/2012 | Tehrani et al. | |
| 8,244,359 | B2 | 8/2012 | Gelfand et al. | |
| 8,255,056 | B2 | 8/2012 | Tehrani | |
| 8,335,567 | B2 | 12/2012 | Tehrani et al. | |
| 8,360,983 | B2 | 1/2013 | Patangay et al. | |
| 8,412,331 | B2 | 4/2013 | Tehrani et al. | |
| 8,467,876 | B2 | 6/2013 | Tehrani | |
| 8,571,662 | B2 | 10/2013 | Hoffer | |
| 8,644,939 | B2 | 2/2014 | Wilson et al. | |
| 8,696,589 | B2 | 4/2014 | Kwok et al. | |
| 8,909,341 | B2 | 12/2014 | Gelfand et al. | |
| 9,108,059 | B2 | 8/2015 | Hoffer | |
| 9,220,898 | B2 | 12/2015 | Hoffer | |
| 9,242,088 | B2 | 1/2016 | Thakkar et al. | |
| 9,333,363 | B2 | 5/2016 | Hoffer et al. | |
| 9,498,627 | B2 | 11/2016 | Rosenberg et al. | |
| 9,538,954 | B2 | 1/2017 | Patangay et al. | |
| 9,545,511 | B2 | 1/2017 | Thakkar et al. | |
| 9,566,436 | B2 | 2/2017 | Hoffer | |
| 9,586,048 | B2 | 3/2017 | Ternes et al. | |
| 9,597,509 | B2 | 3/2017 | Hoffer et al. | |
| 9,744,351 | B1 | 8/2017 | Gelfand et al. | |
| 10,441,213 | B2 | 10/2019 | Thakur et al. | |
| 2005/0085869 | A1 | 4/2005 | Tehrani et al. | |
| 2006/0247729 | A1* | 11/2006 | Tehrani | A61N 1/3601 607/42 |
| 2008/0161878 | A1* | 7/2008 | Tehrani | A61N 1/3601 607/42 |
| 2008/0208282 | A1 | 8/2008 | Gelfand et al. | |
| 2010/0286553 | A1 | 11/2010 | Feler et al. | |
| 2013/0197376 | A1 | 8/2013 | Alt et al. | |
| 2015/0196766 | A1* | 7/2015 | Rosenberg | A61B 5/021 607/42 |
| 2015/0283383 | A1* | 10/2015 | Ternes | A61N 1/3962 607/42 |
| 2016/0135734 | A1 | 5/2016 | Schindhelm et al. | |
| 2017/0290528 | A1 | 10/2017 | Ternes et al. | |
| 2020/0238084 | A1 | 7/2020 | Ignagni | |

* cited by examiner

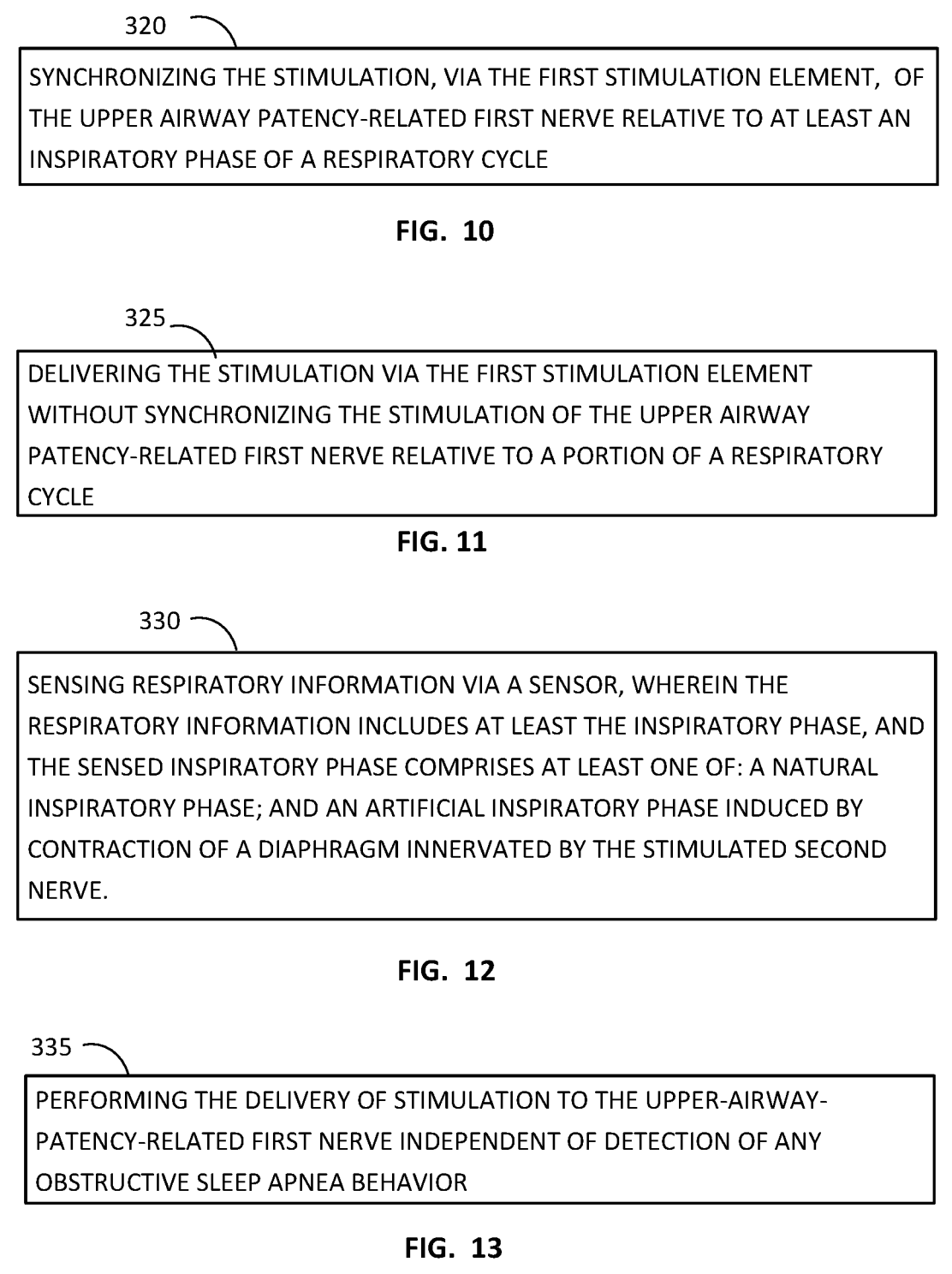

320

SYNCHRONIZING THE STIMULATION, VIA THE FIRST STIMULATION ELEMENT, OF THE UPPER AIRWAY PATENCY-RELATED FIRST NERVE RELATIVE TO AT LEAST AN INSPIRATORY PHASE OF A RESPIRATORY CYCLE

FIG. 10

325

DELIVERING THE STIMULATION VIA THE FIRST STIMULATION ELEMENT WITHOUT SYNCHRONIZING THE STIMULATION OF THE UPPER AIRWAY PATENCY-RELATED FIRST NERVE RELATIVE TO A PORTION OF A RESPIRATORY CYCLE

FIG. 11

330

SENSING RESPIRATORY INFORMATION VIA A SENSOR, WHEREIN THE RESPIRATORY INFORMATION INCLUDES AT LEAST THE INSPIRATORY PHASE, AND THE SENSED INSPIRATORY PHASE COMPRISES AT LEAST ONE OF: A NATURAL INSPIRATORY PHASE; AND AN ARTIFICIAL INSPIRATORY PHASE INDUCED BY CONTRACTION OF A DIAPHRAGM INNERVATED BY THE STIMULATED SECOND NERVE.

FIG. 12

335

PERFORMING THE DELIVERY OF STIMULATION TO THE UPPER-AIRWAY-PATENCY-RELATED FIRST NERVE INDEPENDENT OF DETECTION OF ANY OBSTRUCTIVE SLEEP APNEA BEHAVIOR

FIG. 13

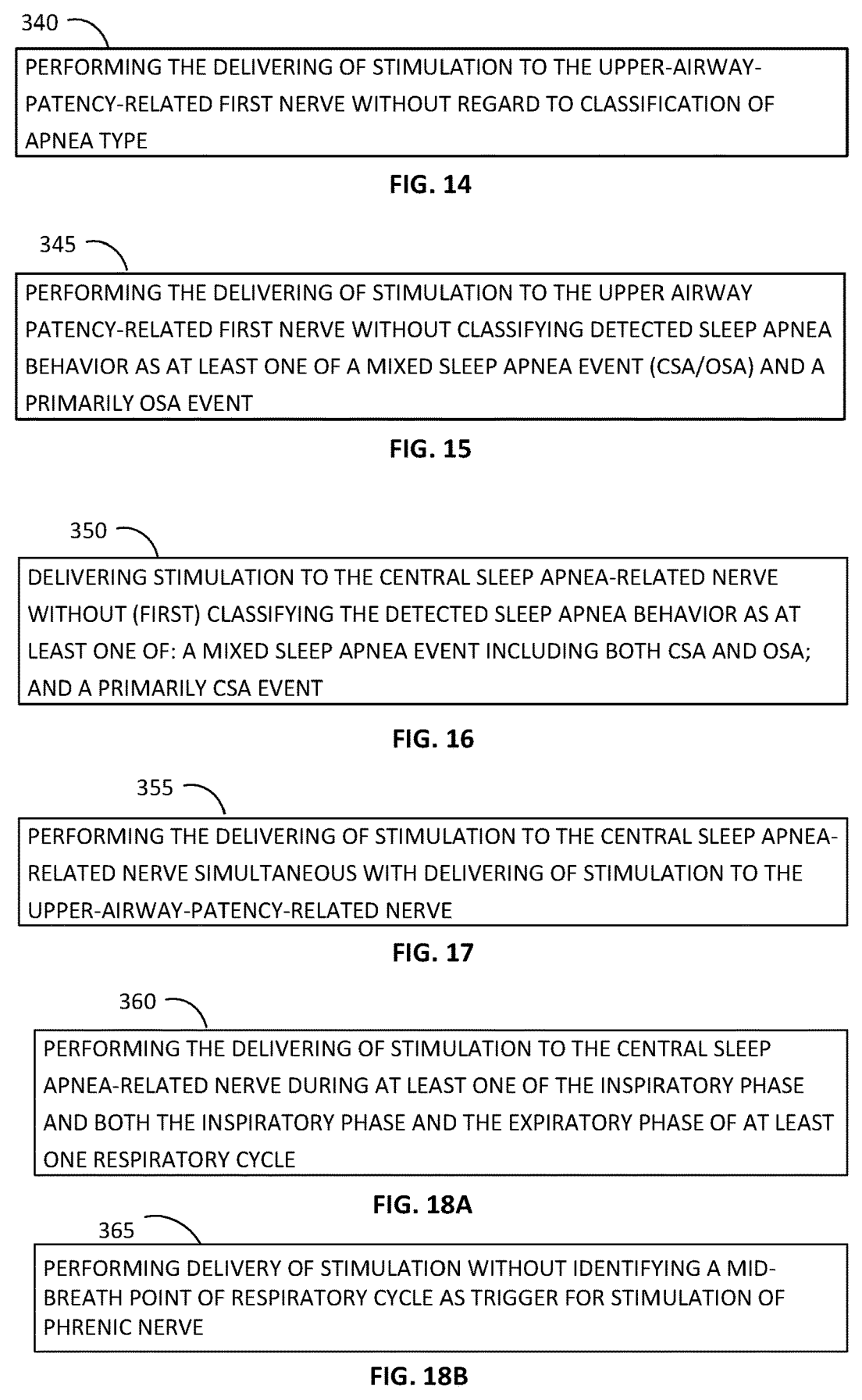

340

PERFORMING THE DELIVERING OF STIMULATION TO THE UPPER-AIRWAY-PATENCY-RELATED FIRST NERVE WITHOUT REGARD TO CLASSIFICATION OF APNEA TYPE

FIG. 14

345

PERFORMING THE DELIVERING OF STIMULATION TO THE UPPER AIRWAY PATENCY-RELATED FIRST NERVE WITHOUT CLASSIFYING DETECTED SLEEP APNEA BEHAVIOR AS AT LEAST ONE OF A MIXED SLEEP APNEA EVENT (CSA/OSA) AND A PRIMARILY OSA EVENT

FIG. 15

350

DELIVERING STIMULATION TO THE CENTRAL SLEEP APNEA-RELATED NERVE WITHOUT (FIRST) CLASSIFYING THE DETECTED SLEEP APNEA BEHAVIOR AS AT LEAST ONE OF: A MIXED SLEEP APNEA EVENT INCLUDING BOTH CSA AND OSA; AND A PRIMARILY CSA EVENT

FIG. 16

355

PERFORMING THE DELIVERING OF STIMULATION TO THE CENTRAL SLEEP APNEA-RELATED NERVE SIMULTANEOUS WITH DELIVERING OF STIMULATION TO THE UPPER-AIRWAY-PATENCY-RELATED NERVE

FIG. 17

360

PERFORMING THE DELIVERING OF STIMULATION TO THE CENTRAL SLEEP APNEA-RELATED NERVE DURING AT LEAST ONE OF THE INSPIRATORY PHASE AND BOTH THE INSPIRATORY PHASE AND THE EXPIRATORY PHASE OF AT LEAST ONE RESPIRATORY CYCLE

FIG. 18A

365

PERFORMING DELIVERY OF STIMULATION WITHOUT IDENTIFYING A MID-BREATH POINT OF RESPIRATORY CYCLE AS TRIGGER FOR STIMULATION OF PHRENIC NERVE

FIG. 18B

368

MAINTAINING THE DELIVERING OF STIMULATION TO THE CENTRAL SLEEP APNEA-RELATED NERVE AT LEAST ONE OF: AT LEAST A PREDETERMINED NUMBER OF RESPIRATORY CYCLES; AND THROUGH THE END OF THE TREATMENT PERIOD

FIG. 19

370

DELIVERING STIMULATION TO THE PHRENIC NERVE COMPRISES DELIVERING A SUPRATHRESHOLD INTENSITY LEVEL OF STIMULATION

FIG. 20

373

PERFORMING THE DELIVERING OF STIMULATION TO THE PHRENIC NERVE WITHOUT HOLDING A BREATH OF THE PATIENT

FIG. 21

375

DETECTING THE CENTRAL SLEEP APNEA BEHAVIOR COMPRISES AT LEAST ONE OF IDENTIFYING A RESPIRATORY AMPLITUDE (DURING AN INSPIRATORY PHASE) OF ZERO AND IDENTIFYING THE RESPIRATORY AMPLITUDE AS LESS THAN A THRESHOLD

FIG. 22

380

IN THE TEMPORARY ABSENCE OF THE INSPIRATORY PHASE DUE TO A CENTRAL SLEEP APNEA EVENT, DELIVERING STIMULATION TO THE HYPOGLOSSAL NERVE VIA A FIRST STIMULATION PROTOCOL WITHOUT SYNCHRONIZATION RELATIVE TO THE INSPIRATORY PHASE, WHEREIN

FIG. 23A

385

DELIVERING STIMULATION VIA THE FIRST STIMULATION PROTOCOL COMPRISES AT LEAST ONE OF: DELIVERING STIMULATION CONTINUOUSLY FOR A SELECTED PERIOD OF TIME; AND DELIVERING STIMULATION ACCORDING TO A CYCLIC PATTERN MIMICKING AN INTRINSIC RESPIRATORY CYCLE

FIG. 23B

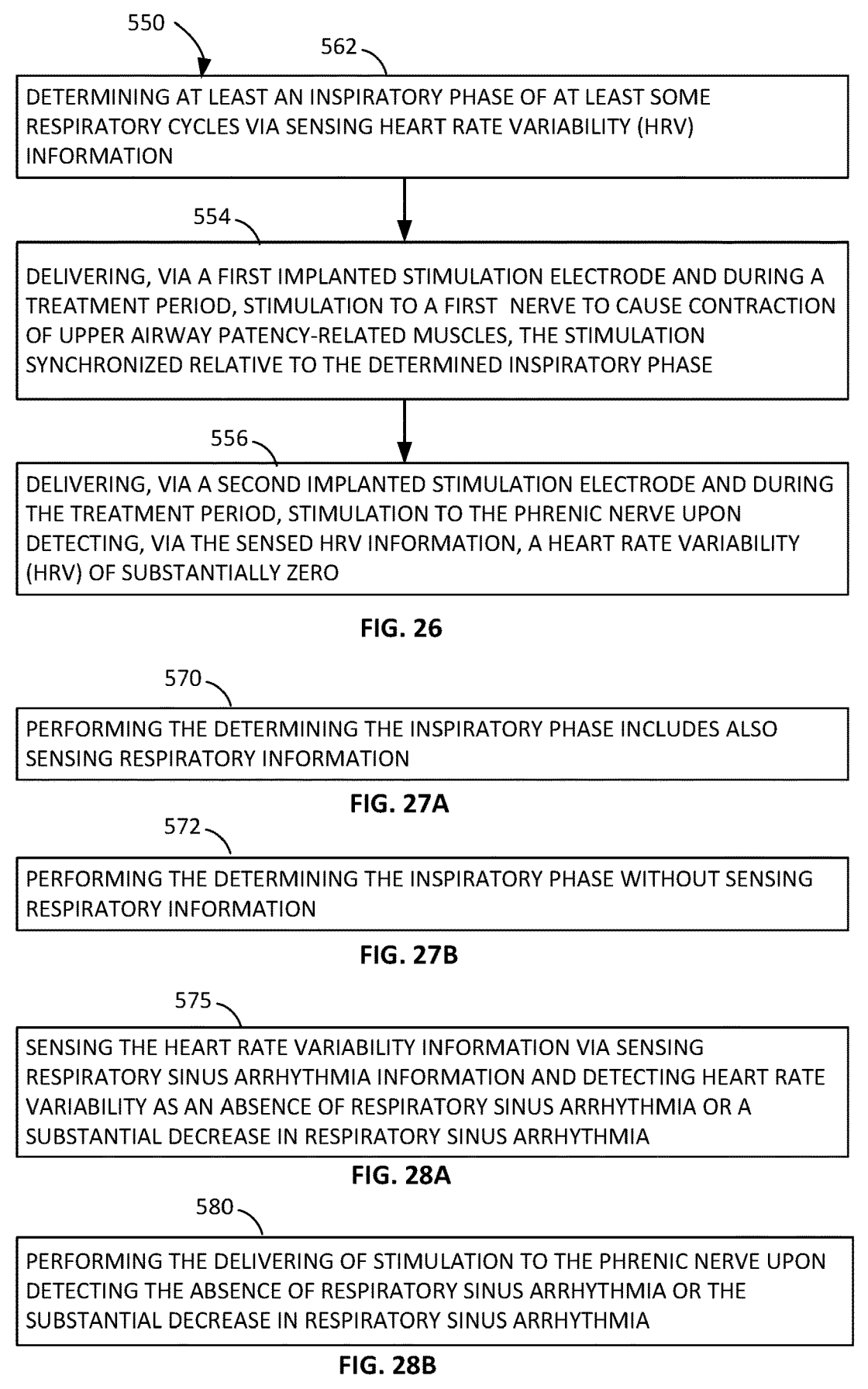

550

562 DETERMINING AT LEAST AN INSPIRATORY PHASE OF AT LEAST SOME RESPIRATORY CYCLES VIA SENSING HEART RATE VARIABILITY (HRV) INFORMATION

↓

554 DELIVERING, VIA A FIRST IMPLANTED STIMULATION ELECTRODE AND DURING A TREATMENT PERIOD, STIMULATION TO A FIRST NERVE TO CAUSE CONTRACTION OF UPPER AIRWAY PATENCY-RELATED MUSCLES, THE STIMULATION SYNCHRONIZED RELATIVE TO THE DETERMINED INSPIRATORY PHASE

↓

556 DELIVERING, VIA A SECOND IMPLANTED STIMULATION ELECTRODE AND DURING THE TREATMENT PERIOD, STIMULATION TO THE PHRENIC NERVE UPON DETECTING, VIA THE SENSED HRV INFORMATION, A HEART RATE VARIABILITY (HRV) OF SUBSTANTIALLY ZERO

FIG. 26

570 PERFORMING THE DETERMINING THE INSPIRATORY PHASE INCLUDES ALSO SENSING RESPIRATORY INFORMATION

FIG. 27A

572 PERFORMING THE DETERMINING THE INSPIRATORY PHASE WITHOUT SENSING RESPIRATORY INFORMATION

FIG. 27B

575 SENSING THE HEART RATE VARIABILITY INFORMATION VIA SENSING RESPIRATORY SINUS ARRHYTHMIA INFORMATION AND DETECTING HEART RATE VARIABILITY AS AN ABSENCE OF RESPIRATORY SINUS ARRHYTHMIA OR A SUBSTANTIAL DECREASE IN RESPIRATORY SINUS ARRHYTHMIA

FIG. 28A

580 PERFORMING THE DELIVERING OF STIMULATION TO THE PHRENIC NERVE UPON DETECTING THE ABSENCE OF RESPIRATORY SINUS ARRHYTHMIA OR THE SUBSTANTIAL DECREASE IN RESPIRATORY SINUS ARRHYTHMIA

FIG. 28B

MULTIPLE TYPE SLEEP APNEA

CROSS-REFERENCE TO RELATED APPLICATION

This application is a utility application which claims the benefit of U.S. Patent Application Ser. No. 62/760,097 filed Nov. 13, 2018, and incorporated herein by reference.

BACKGROUND

A significant portion of the population suffers from various forms of sleep apnea. In some patients, more than one type of sleep apnea may be exhibited.

BRIEF DESCRIPTION OF THE DRAWINGS

FIG. 10 is a diagram schematically representing at least a portion of an example method of treating sleep apnea.

FIG. 11 is a diagram schematically representing at least a portion of an example method of treating sleep apnea.

FIG. 12 is a diagram schematically representing sensing in association with an example method of treating sleep apnea.

FIG. 13 is a diagram schematically representing at least a portion of an example method of treating sleep apnea.

FIG. 14 is a diagram schematically representing an example method of treating sleep apnea, including stimulation.

FIG. 15 is a diagram schematically representing an example method of treating sleep apnea, including stimulation for at least a multiple-type apnea event.

FIG. 16 is a diagram schematically representing an example method of treating sleep apnea, including stimulation for at least a multiple-type apnea event.

FIG. 17 is a diagram schematically representing an example method of treating sleep apnea, including stimulation of both a central sleep apnea (CSA) related nerve and an obstructive sleep apnea (OSA) related nerve.

FIG. 18A is a diagram schematically representing an example method of treating sleep apnea, including stimulation during specific phases of a respiratory cycle.

FIG. 18B is a diagram schematically representing an example method of treating sleep apnea, including stimulation.

FIG. 19 is a diagram schematically representing an example method of treating sleep apnea, including stimulation of a central sleep apnea-related nerve.

FIG. 20 is a diagram schematically representing an example method of treating sleep apnea, including stimulation of a central sleep apnea-related nerve.

FIG. 21 is a diagram schematically representing an example method of treating sleep apnea, including stimulation of a central sleep apnea-related nerve.

FIG. 22 is a diagram schematically representing an example method of detecting central sleep apnea behavior.

FIG. 23A is a diagram schematically representing an example method of treating sleep apnea, including stimulation of an upper airway patency-related nerve.

FIG. 23B is a diagram schematically representing an example method of treating sleep apnea, including stimulation according to a first stimulation protocol.

FIG. 26 is a diagram schematically representing an example method of treating multiple-type sleep apnea.

FIG. 27A is a diagram schematically representing an example method of treating sleep apnea, including determining an inspiratory phase of a respiratory cycle.

FIG. 27B is a diagram schematically representing an example method of treating sleep apnea, including determining an inspiratory phase of a respiratory cycle.

FIG. 28A is a diagram schematically representing an example method of treating sleep apnea, including sensing heart rate variability.

FIG. 28B is a diagram schematically representing an example method of treating sleep apnea, including stimulation of a phrenic nerve.

DETAILED DESCRIPTION

Figure 1:
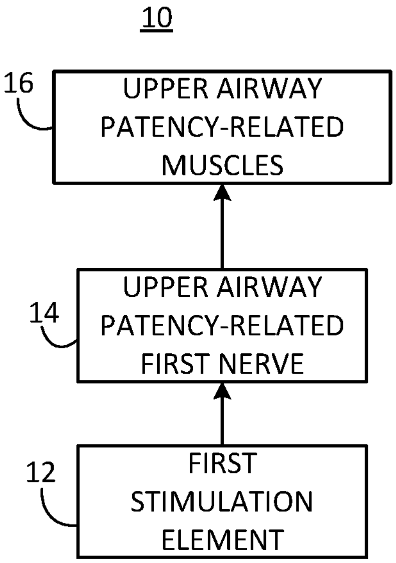
FIG. 1 is a diagram schematically representing an example method and/or example device for stimulating upper airway patency-related muscles.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure are directed to sleep disordered breathing (SDB) care, which may include treating multiple types of sleep apnea, among other aspects of SDB care.

In some examples, a method comprises delivering, via a first stimulation element and during a treatment period, stimulation to an upper airway patency-related first nerve to cause contraction of upper airway patency-related muscles.

In some examples, a method comprises delivering, via a second stimulation element and during a treatment period, stimulation to a central sleep apnea-related second nerve. In some such examples, the stimulation is delivered upon detecting central sleep apnea behavior while in some such examples the stimulation is delivered upon other criteria and/or additional criteria.

In some examples, both of the above-described methods may be performed, wherein delivering stimulation to the upper airway patency-related first nerve is performed independently of a decisional process and/or trigger to deliver stimulation to the different central sleep apnea-related second nerve.

In some examples, a single implantation method may be performed to treat multiple types of sleep apnea. In some such examples, at the time of a first implantation, it may not be known how many types and/or all of the types of sleep apnea which are to be treated. However, via at least some examples of the present disclosure in which a device has been implanted and used to treat at least one type of sleep apnea, the same implanted device may be used to treat at least a second type of sleep apnea. In one aspect, this example arrangement may avoid having to later perform a second implantation to treat the second type of sleep apnea, which sometimes may be recognized solely after treatment of a first type of sleep apnea.

In some examples, a single implant device may be used to treat obstructive sleep apnea and then also used to later treat central sleep apnea which has been recognized after (or during) treatment of obstructive sleep apnea via the single implant device. In some such examples, the central sleep apnea behavior may develop, or be first recognized, sometime after (but not be caused by) implantation and use of the single implant device. In some such examples, the single implant device (which was first used to treat obstructive sleep apnea) may include sensing, communication, processing features and/or the like which may at least partially implement the recognition of central sleep apnea and which may then be used to also treat central sleep apnea in addition to treating obstructive sleep apnea. In some instances, these example arrangements may be useful in situations in which central sleep apnea led to obstructive sleep apnea.

In some examples, a single implant device may be used to treat central sleep apnea and then also used to later treat obstructive sleep apnea which has been recognized after (or during) treatment of central sleep apnea via the single implant device. In some such examples, the obstructive sleep apnea may develop, or be first recognized, sometime after (but not be caused by) implantation and use of the single implant device. In some such examples, the single implant device (which was first used to treat central sleep apnea) may include sensing, communication, processing features and/or the like which may at least partially implement the recognition of obstructive sleep apnea and which may then be used to also treat obstructive sleep apnea in addition to treating central sleep apnea. In some such examples, the single implant device may be used to treat central sleep apnea and then later (and also) treat obstructive sleep apnea when the central sleep apnea led to obstructive sleep apnea. For instance, during one or more central sleep apnea events (in the absence of treatment via the single implant device), airway muscle tone may be reduced and therefore lead to airway obstruction as respiratory effort is restored. However, via at least some examples of the present disclosure of treating both central sleep apnea and obstructive sleep apnea, upper airway patency is maintained, thereby preventing its collapse in the event of potential central sleep apnea behavior. Of course, in some examples, stimulation of a central sleep apnea-related nerve may be performed in a manner to maintain respiratory drive and prevent central sleep apnea.

Accordingly, an example single implant device may provide the capability of treating a second type of sleep apnea which is first recognized, and/or which develops, after treatment of a first type of sleep apnea via an example single implant device. Moreover, the single implant device may avoid the invasive and disruptive aspects of a later, second implantation procedure in the event a first implant device was originally adapted to treat solely one type of sleep apnea. Such invasive, disruptive aspects may include opening a second pectoral pouch for a pulse generator or re-opening an existing pectoral pouch, as well as the creating of a second tunnel (or attempt at using an existing tunnel) between the pectoral pouch and a head-neck region at which a stimulation electrode is to be implanted. The invasive and disruptive aspects may necessarily include the general risks of undergoing any surgery and possible general complications arising therefrom.

It will be understood that in some examples, the various example elements, example devices, and example methods for delivering stimulation to the upper airway patency-related nerve can be performed solely to treat obstructive sleep apnea without intentionally attempting to treat central sleep apnea. Conversely, it will be understood that in some examples, the various example elements, example devices, and example methods for delivering stimulation to the central sleep apnea-related nerve can be performed solely to treat central sleep apnea without intentionally attempting to treat obstructive sleep apnea.

It will be understood that, at least for purposes of the examples of the present disclosure, the phrenic nerve is not considered an upper airway patency-related nerve and the hypoglossal nerve is not considered a central sleep apnea-related nerve.

These examples, and additional examples, are further described in association with at least FIGS. 1-38C.

FIG. 1 is a block diagram schematically representing an example arrangement 10 which may comprise an example device and/or example method to deliver stimulation to an upper airway patency-related nerve. As shown in FIG. 1, a device 10 may comprise a first stimulation element 12 coupled to an upper airway patency-related first nerve 14, which innervates upper airway patency-related muscles 16. In some examples, the first stimulation element 12 may comprise an implantable stimulation element, which in some examples may comprise an implantable stimulation electrode. In some examples, the term "coupled to" may comprise a direct physical and electrical connection relative to a target nerve (and/or target muscle) such as via a cuff electrode, while in some examples the term "coupled to" may comprise an indirect connection in which a stimulation element may be adjacent to, but spaced apart from a target nerve and/or target muscle.

In some examples, the implantable stimulation element may be powered by and/or controlled by a pulse generator, which also may be implantable. At least some example pulse generators are described later in association with at least FIG. 29. At least some example implementations of device 10 are further described later in association with at least FIGS. 6, 29, 30A-31, with such examples also comprising a pulse generator in at least some instances.

Figure 2:
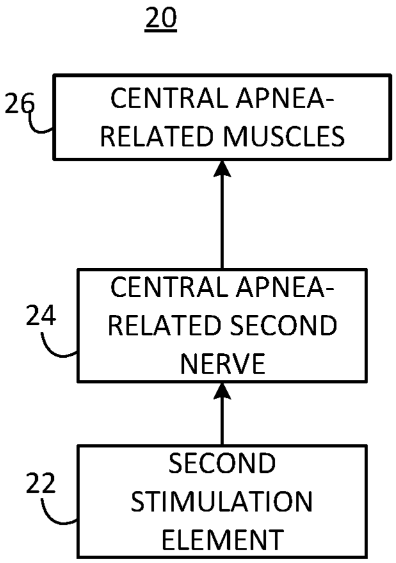
FIG. 2 is a diagram schematically representing an example method and/or example device for stimulating central apnea-related muscles.

FIG. 2 is a block diagram schematically representing an example arrangement 20, which may comprise an example device and/or example method to deliver stimulation to a central-sleep-related second nerve. As shown in FIG. 2, a device 20 comprises a second stimulation element 22 coupled to a central sleep apnea-related second nerve 24, which innervates upper airway patency-related muscles 26. In some such examples, the term "coupled to" may comprise the same scope and meaning as described above. In some examples, the second stimulation element 22 and/or associated pulse generator may comprise at least some of substantially the same features and attributes as the stimulation element 12 (and associated pulse generator) as previously described in association with FIG. 1. The pulse generator used to power and/or control the second stimulation element 42 may the same pulse generator, or a different pulse generator, than the pulse generator used to deliver power and/or control the first stimulation element 22. At least some example implementations of device 20 are further described later in association with at least FIGS. 30A-31.

Figure 3:
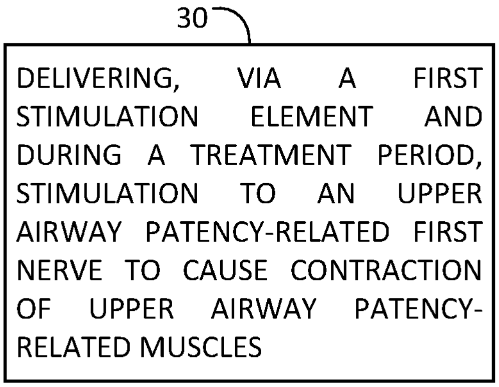
FIG. 3 is a diagram schematically representing an example method for stimulating upper airway patency-related muscles.

As shown in FIG. 3, in some examples a method 30 comprises delivering, via a first stimulation element (e.g. 12 in FIG. 1) and during a treatment period, stimulation to an upper airway patency-related first nerve (e.g. 14 in FIG. 1) to cause contraction of upper airway patency-related muscles (e.g. 16 in FIG. 1). In some such examples, the contraction comprises a suprathreshold stimulation, which is in contrast to a subthreshold stimulation of such muscles. In one aspect, a suprathreshold intensity level corresponds to a stimulation energy greater than the nerve excitation threshold, such that the suprathreshold stimulation may provide for maximum upper-airway clearance (i.e. patency) and obstructive sleep apnea therapy efficacy.

In some examples, the treatment period may comprise a period of time beginning with the patient turning on the therapy device and ending with the patient turning off the device. In some examples, the treatment period may comprise a selectable, predetermined start time (e.g. 10 p.m.) and selectable, predetermined stop time (e.g. 6 a.m.). In some examples, the treatment period may comprise a period of time between an auto-detected initiation of sleep and auto-detected awake-from-sleep time. With this in mind, the treatment period corresponds to a period during which a patient is sleeping such that the stimulation of the upper airway patency-related nerve and/or central sleep apnea-related nerve is generally not perceived by the patient and so that the stimulation coincides with the patient behavior (e.g. sleeping) during which the sleep disordered breathing behavior (e.g. central or obstructive sleep apnea) would be expected to occur.

In some examples, the stimulation is applied during some of the treatment period without being delivered throughout the treatment period. Stated differently, in some examples stimulation may be performed during some portions of the treatment period but not during other portions of the same treatment period.

In some examples, stimulation applied during the treatment period may comprise stimulation delivered throughout the treatment period. In some such examples, stimulation delivered throughout the treatment period may comprise stimulation being delivered throughout the entire treatment period. In some such examples, the term "throughout the entire" may comprise stimulation being performed in 100 percent of the treatment period. However, it will be understood that in some examples some startup routines, shutdown routines are not considered part of the 100 percent.

In some examples, stimulation being delivered throughout the treatment period comprises stimulation delivered throughout substantially the entire treatment period. In some such examples, in this context, the term "substantially the entire" comprises at least 70 percent, at least 80 percent, at least 90 percent, or at least 95 percent of the entire treatment period.

In some such examples, stimulation of the upper airway patency-related nerve which is maintained during the treatment period may be referred to as being "on-going" in the treatment period but not continuous. For instance, the on-going stimulation may be implemented via a duty cycle, train of pulses, etc. such that the stimulation need not be one hundred percent continuous within a given respiratory cycle. Rather, in some such examples, the term "on-going" stimulation may refer to stimulation which does not start and/or stop based on occurrence of some event such as a controller signal to start stimulation of upper airway patency-related nerve just prior to stimulation of central-apnea-related nerve or a controller signal to stop stimulation of an upper airway patency-related nerve just after stimulation of a central sleep apnea-related nerve.

In some examples, such on-going stimulation during the treatment period may be considered preventative with respect to obstructive sleep apnea.

To avoid enabling stimulation prior to the patient falling asleep, stimulation can be enabled after expiration of a timer started by the patient (to enable therapy with a remote control), or enabled automatically via sleep stage detection, such as at least the later described examples in association with FIGS. 32-37. To avoid continuing stimulation after the patient wakes, stimulation can be disabled by the patient using a remote control, or automatically via sleep stage detection. Accordingly, in at least some examples, these periods may be considered to be outside of the treatment period or may be considered as a startup portion and wind down portion, respectively, of a treatment period.

In some examples, stimulation of an upper airway patency-related nerve may be performed via open loop stimulation. In some examples, the open loop stimulation may refer to performing stimulation without use of any sensory feedback of any kind relative to the stimulation.

In some examples, the open loop stimulation may refer to stimulation performed without use of sensory feedback by which timing of the stimulation (e.g. synchronization) would otherwise be determined relative to respiratory information (e.g. respiratory cycles). However, in some such examples, some sensory feedback may be utilized to determine, in general, whether the patient should receive stimulation based on a severity of sleep apnea behavior.

Conversely, in some examples, stimulation of an upper airway patency-related nerve may be performed via closed loop stimulation. In some examples, the closed loop stimulation may refer to performing stimulation at least partially based on sensory feedback regarding parameters of the stimulation and/or effects of the stimulation.

In some examples, the closed loop stimulation may refer to stimulation performed via use of sensory feedback by which timing of the stimulation (e.g. synchronization) is determined relative to respiratory information (e.g. respiratory cycles). In addition, in some such examples, some sensory feedback may be utilized to determine, in general, whether the patient should receive stimulation based on a severity of sleep apnea behavior. In other words, upon sensing that a certain number of sleep apnea events are occurring, the device may implement stimulation.

Figure 4:
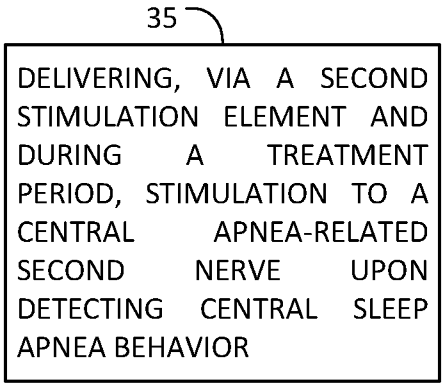
FIG. 4 is a diagram schematically representing an example method for stimulating central apnea-related muscles.

As shown in FIG. 4, in some examples, a method 35 may comprise delivering, via a second stimulation element and during a treatment period, stimulation to a central sleep apnea-related second nerve (e.g. 50 in FIG. 2) upon detecting central sleep apnea behavior. In some examples, the detection of a central sleep apnea event may correspond to and/or comprise detection of a lack of respiratory drive, which may manifest itself as no respiratory effort. In some examples, the treatment period of method 35 may comprise substantially the same treatment period as for method 30, while in some examples, the treatment period of method 35 may comprise a different treatment period than that of method 30.

In some examples, the stimulation applied via method 35 (FIG. 4) may be delivered according to a pattern which resembles the patient's natural respiratory cycle. In some such examples, a natural respiratory cycle also may sometimes be referred to as an intrinsic respiratory cycle. In these examples, stimulation of the central sleep apnea-related nerve (e.g. phrenic nerve) generally coincides with (e.g. is synchronous with) the inspiratory phase of a respiratory cycle.

With further reference to the method at 35 of FIG. 4, in some examples sensed respiratory information may indicate an absence of respiratory effort according to a sensed respiratory amplitude being less than a threshold or less than a moving average of previous respiratory amplitudes. In some such examples, stimulation of a central sleep apnea-related nerve is delivered to cause an inspiratory and expiratory period with characteristics similar to the patient's normal inspiratory period by modulating the stimulation amplitude during the respiratory cycle according to the sensed respiratory response of the current and/or previous cycles.

Further example implementations of stimulation of a central sleep apnea-related nerve and/or associated sensing of respiratory information are described later in association with various example throughout the present disclosure.

In some examples, stimulation of a central sleep apnea-related nerve may be performed in periods of unstable breathing even when there is not a lack of respiratory drive, i.e. even when at least some respiratory effort is present. In some such examples, stimulation may be delivered to the central sleep apnea-related nerve during inspiration to prolong the inspiratory period and thereby attempt to stabilize respiration. Such stimulation is not delivered during an expiratory phase of the respiratory cycle, at least in some examples.

In some examples, performing stimulation of a central sleep apnea-related nerve (e.g. phrenic nerve) on an as-needed basis may preserve therapy response (i.e. by avoid desensitization and/or fatigue) and may enhance battery longevity of the device, such as the pulse generator powering the stimulation element 22.

Figure 5A:
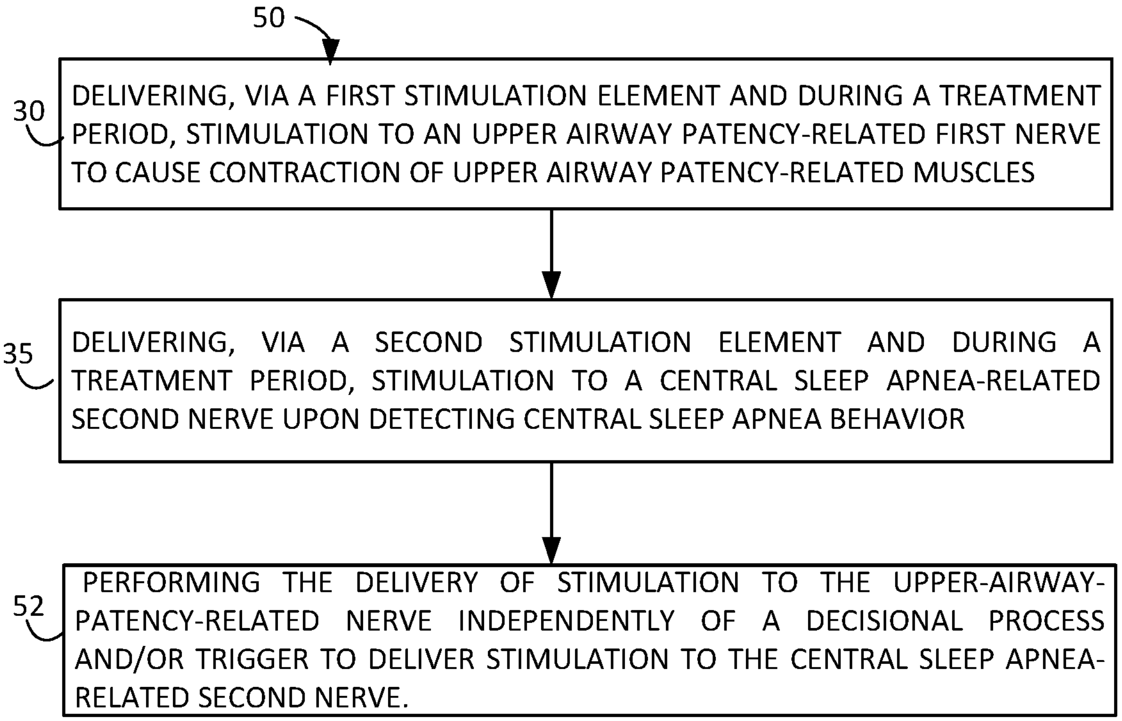
FIG. 5A is a flow diagram schematically representing an example method for treating multiple-type sleep apnea.

In some examples, both the action represented at 30 in FIG. 3 and at 35 in FIG. 4 may both be performed to comprise an example method 50 as shown in FIG. 5A. As further shown at 52 in FIG. 5A, method 50 may further comprise performing the delivery of stimulation to the upper airway patency-related first nerve (e.g. 14 in FIG. 1) independently of a decisional process and/or of a trigger to deliver stimulation to the different central sleep apnea-related second nerve. As previously noted, the stimulation of the upper airway patency-related nerve 14 during at least a portion of the treatment period does not depend on a decisional process and/or trigger to deliver stimulation to the central sleep apnea-related nerve 24. Accordingly, in at least some examples, the stimulation of the upper airway patency-related first nerve is performed without regard to whether or not any stimulation is delivered to the central sleep apnea-related second nerve. It will be understood that, in at least some examples with respect to at least method 50, the treatment period (at 30 in FIG. 3, 5A) of stimulating the upper airway patency-related nerve is the same treatment period (at 35 in FIGS. 4, 5A) used for stimulation of the central sleep apnea-related nerve (upon detecting central sleep apnea behavior).

Via at least some of these example arrangements, method 50 does not attempt to distinguish between obstructive sleep apnea and central sleep apnea, but rather, potential or actual obstructive sleep apnea (OSA) is treated via stimulation of an upper airway patency-related nerve during the treatment period (whether or not an obstructive sleep apnea events are occurring) while central sleep apnea is treated via stimulation of a central sleep apnea-related nerve just when central sleep apnea events or behavior occurs.

Accordingly, in at least some examples stimulation for central sleep apnea is performed on an as-needed basis within the treatment period even though stimulation (of an upper airway patency-related nerve) for obstructive sleep apnea may be performed in a more regular manner during the treatment period, and possibly throughout the treatment period as previously described above in association with at least FIGS. 1 and 3. In some examples, it is possible that no stimulation (of a central sleep apnea-related nerve) to treat central sleep apnea may occur in any given treatment period if no central sleep apnea behavior is detected during that treatment period.

In some examples, one trigger for treating central sleep apnea may comprise a detection a central sleep apnea event or behavior, which in some examples, may comprise a detection of a lack of respiratory drive. In some such examples, the detection of lack of respiratory drive may comprise detection of an absence or nearly complete absence of an inspiratory phase of at least some respiratory cycles.

Figure 5B:
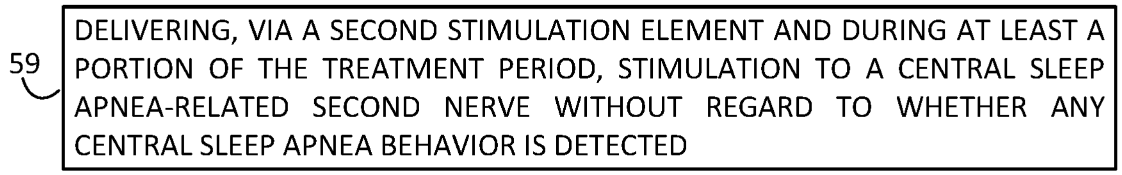
FIG. 5B is a flow diagram schematically representing an example method for treating multiple-type sleep apnea.

In some examples, method 50 in FIG. 5A may be modified by substituting the action 59 shown in FIG. 5B for the action 35 in FIG. 5A, wherein at 59 method 50 may comprise delivering, via a second stimulation element and during the treatment period, stimulation to a central sleep apnea-related nerve without regard to whether any central sleep apnea behavior is detected. For instance, in some such examples, this stimulation may be delivered intermittently on a random basis or intermittently according to regular interval (e.g. every 5 minutes, every 10 minutes, etc.). In some examples, stimulation is delivered to the central sleep apnea-related nerve throughout the treatment period.

With reference to at least FIG. 5A, in some examples in which stimulation is delivered to a central sleep apnea-related nerve, a device/method comprises delivering stimulation to the upper airway patency-related first nerve via: synchronizing the stimulation of the upper airway patency-related nerve relative to sensed natural inspiratory phase of respiratory cycles throughout the treatment period; or triggering the delivery of the stimulation of the upper airway patency-related nerve relative to the delivery of stimulation to the central sleep apnea-related second nerve. In some such examples of delivering stimulation to the upper airway patency-related nerve which is triggered by delivery of stimulation to the central sleep apnea-related nerve (and therefore not triggered based on sensing an inspiratory phase), this arrangement may ensure opening the upper airway just before expected contraction of the diaphragm, which will cause negative pressure to draw air into and through the upper airway. If the upper airway were not sufficiently patent (i.e. open) upon the application of such negative pressure, then the upper airway might collapse. With this in mind, in some situations in which sensing of the inspiratory phase (to trigger stimulation of the upper airway patency-related nerve) may be unavailable, inadequate, etc., then using the delivery of stimulation of a central sleep apnea-related nerve may serve as a more reliable basis on which to trigger stimulation of the upper airway patency-related nerve, and thereby ensure patency of the upper airway prior to inspiration occurring.

In some such examples in which triggering the delivery of the stimulation of the upper airway patency-related nerve is based on delivery of stimulation to the central sleep apnea-related nerve, stimulation of the upper airway patency-related nerve may be delivered prior to delivery of the stimulation of the central sleep apnea-related second nerve and/or may be delivered to extend after (e.g. continue) delivery of the stimulation of the central sleep apnea-related second nerve.

Whether implemented via action 59 (FIG. 5B) or via other methods and/or devices, some examples may comprise preventing central apnea events. In some such examples, prevention may be implemented via stimulating the phrenic nerve during a sensed inspiratory period to ensure stabilization of respiration. For instance, the stimulation may extend beyond the sensed inspiratory period until nominal respiratory amplitude and/or inspiratory period is met. In some cases, these nominal values are determined by the mean of the patient's respiratory cycle from periods of normal breathing. In some cases, these nominal values are determined by the cycle of maximal amplitude of a patient's Cheyne Stokes breathing pattern. In some such examples for preventing central sleep apnea, stimulation of the phrenic nerve is delivered during sensed inspiratory periods which are determined by an increase in heart rate over the average of a previous period. Meanwhile, in some examples sensed expiratory periods may be determined by a decrease in heart rate over the average of the previous period, a respiratory rate may be determined by the period of the cyclical change in heart rate, and the start of the inspiratory period may then be determined by a fraction of the respiratory period starting from the end of the expiratory period. In some examples, a start of inspiratory period may be determined as the end of the expiratory period plus thirty percent of a respiratory period. The end of the inspiratory period may be determined by a fraction of the respiratory period starting from the start of the inspiratory period. At least some related information and additional information regarding determination of various portions of respiratory cycle (e.g. period) are described below throughout various examples of the present disclosure, such as but not limited to, FIGS. 18A-28B.

Figure 6:
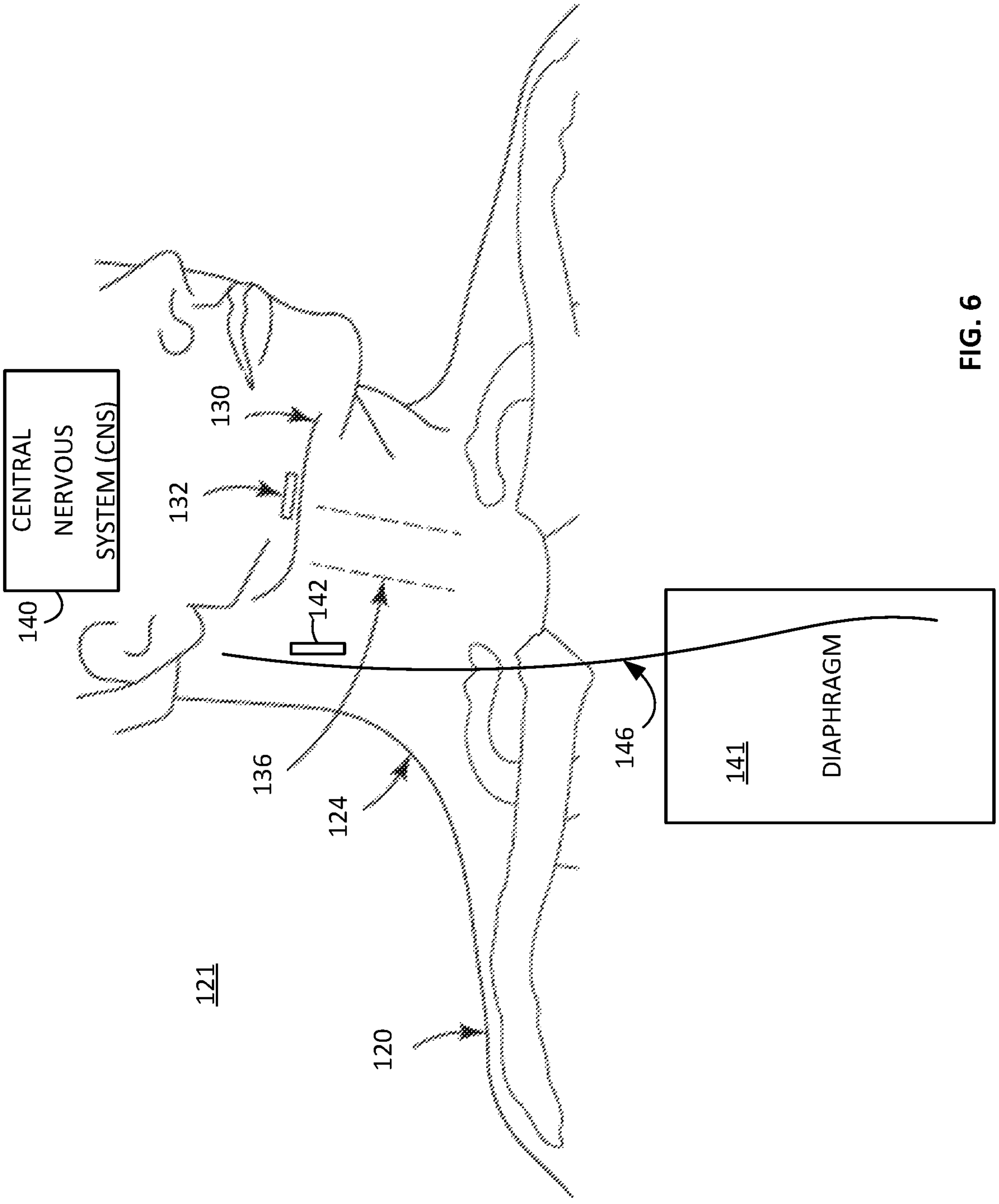
FIG. 6 is a diagram schematically representing an example arrangement of a stimulation element relative to central sleep apnea-related nerves and muscles.

FIG. 6 is a diagram schematically representing an upper portion of a patient's body 120 and an example arrangement 121 and/or example method to treat sleep apnea. As shown in FIG. 6, a stimulation element 132 is implanted within a head/neck region 124 of the patient, according to one example of the present disclosure. As shown in FIG. 6, in some examples, stimulation element 132 is implanted subcutaneously in proximity to a target nerve 130. Stimulation of the target nerve 130 via stimulation element 132 causes contraction of at least some muscles innervated via the target nerve 130. In some examples, the target nerve 130 comprises an upper airway patency-related nerve, such as but not limited to the hypoglossal nerve. In some examples, various aspects regarding the implantation and deployment of stimulation element 132 are described later in association with various example implementations. In some examples, stimulation element 132 and arrangement 121 may comprise one example implementation of stimulation element 12 and device 10, respectively, which was previously described in association with at least FIGS. 1, 3, 5A-5B.

As further shown in FIG. 6, in some examples, a stimulation element 142 is implanted subcutaneously in proximity to a target nerve 146. Stimulation of the target nerve 146 via stimulation element 142 causes contraction of at least some muscles innervated via the target nerve 146. In some examples, the target nerve 146 comprises a central sleep apnea-related nerve, such as but not limited to the phrenic nerve which innervates diaphragm 141. Stimulation of the phrenic nerve may simulate a signal normally sent by the central nervous system (CNS) 140 to maintain respiratory drive. In some examples, various aspects regarding the implantation and deployment of stimulation element 142 are described later in association with at least FIGS. 30A-31. In some examples, stimulation element 142 and arrangement 121 may comprise one example implementation of stimulation element 22 and device 20, respectively, which was previously described in association with at least FIGS. 2, 4, 5A-5B.

With regard to FIG. 6, it will be understood that the various stimulation elements 132, 142 may be positioned in locations along the respective target nerves 130, 146 different from shown in FIG. 6 and that in some examples the various stimulation elements 132, 142 may be positioned in locations adjacent other nerves responsible for treating obstructive sleep apnea and central sleep apnea and behaviors involving both obstructive and sleep apnea. In some examples, the stimulation elements 132, 142 may be positioned in location to directly stimulate a target muscle (e.g. genioglossus muscle, etc. or diaphragm 141) instead of stimulating an associated nerve. Moreover, the depiction of stimulation elements 132, 142 in FIG. 6 is a schematic representation such that elements 132, 142 may represent a cuff electrode or other types of electrodes, stimulation elements, etc., at least some of which are described later in association with FIGS. 30A-31. It will be understood that in some examples, each given stimulation element 132, 142 (including the later example implementations) also may comprise an array of elements, which may be arranged in a wide variety of configurations, such as but not limited to a row, rows, staggered configurations, grid (2×2, 3×3), and combinations thereof.

Figure 7A:
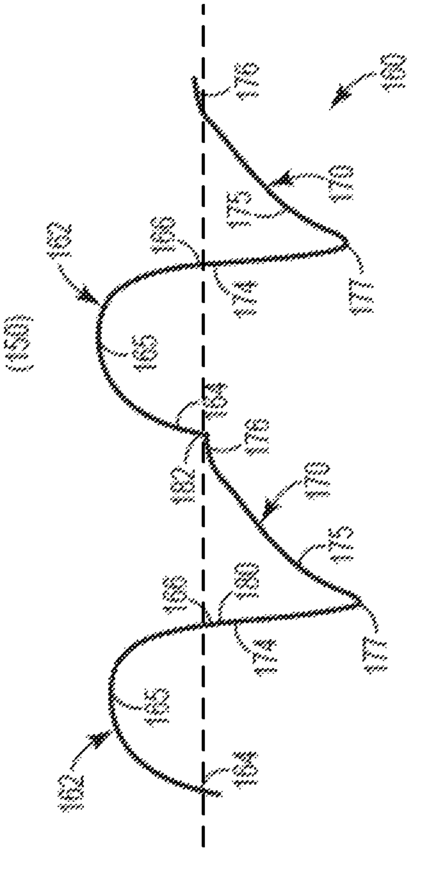
FIG. 7A is diagram schematically representing an example respiratory waveform.

FIG. 7A is a diagram schematically representing a respiratory cycle 150 including an inspiratory phase 162 and an expiratory phase 170. The inspiratory phase 162 includes an initial portion 164, intermediate portion 165, and end portion 166 while expiratory phase 170 includes an initial portion 174, intermediate portion 175, end portion 176, and an expiratory peak 177. A first transition 180 occurs at a junction between the end inspiratory portion 166 and the initial expiratory portion 174 while a second transition 182 occurs at a junction between the end expiratory portion 176 and the initial inspiratory portion 164.

Figure 7B:
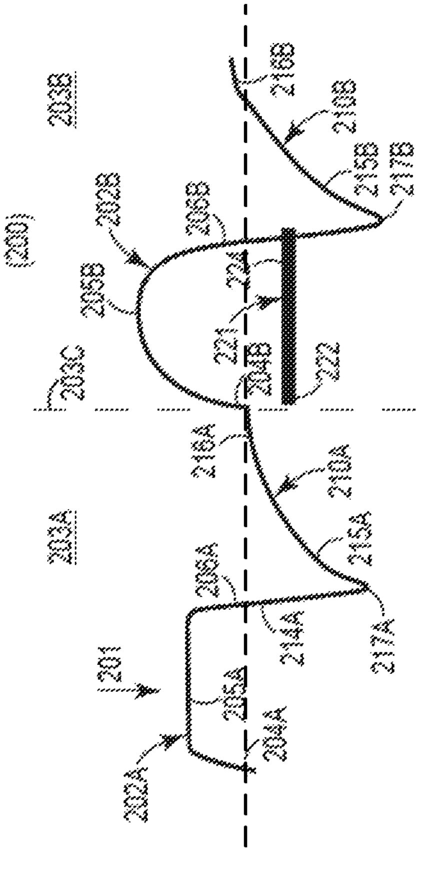
FIG. 7B is diagram schematically representing an example respiratory waveform including an obstructive apnea event during an inspiratory phase and stimulation during a subsequent inspiratory phase of a respiratory cycle.

FIG. 7B is a diagram 200 illustrating a disordered breathing pattern 203A and an example treated breathing pattern 203B as separated by dashed line 203C. As shown in FIG. 7B, disordered breathing pattern 203A reflects the presence of a flow limitation in the upper airway that occurs predominantly during the inspiratory phase of a respiratory cycle, and may be representative of obstructive sleep apnea. The inspiratory phase 202A includes an initial portion 204A, an intermediate portion 205A, and an end portion 206A while the expiratory phase 210A includes an initial portion 214A, intermediate portion 215A, peak 217A, and end portion 216A. In one aspect, intermediate portion 205A of inspiratory phase 202A forms a generally flat or horizontal shape corresponding to a substantially truncated amplitude (as compared to a normal breathing pattern, such as FIG. 7A) and that reflects the occurrence of a flow limitation (symbolically represented by arrow 201) in the upper airway during inspiration. However, as shown in FIG. 7B, via application of stimulation (symbolically represented by bar 221) to an upper airway patency-related nerve (e.g. 14 in FIG. 1; 130 in FIG. 6), upper airway patency and breathing is restored as represented by treated breathing pattern 202B in which intermediate portion 205B of inspiratory phase 202B resumes a generally parabolic shape corresponding to a generally normal amplitude and that represents amelioration of the flow limitation. In one embodiment, the stimulation is represented by bar 221, which extends from a first end 222 to a second end 224, with the stimulation substantially coinciding with the entire duration of the inspiratory phase 202B. As shown in FIG. 3, the stimulation 221 terminates prior to the expiratory phase 210B. However, as previously noted, in some examples the delivered stimulation may extend more than or less than the entire duration of inspiratory phase 202B.

It will be understood that, in one example, the detection of flow limitations and/or associated apneas), as well as the detection of the beginning and end of the respective inspiratory and expiratory phases of the respiratory cycle to enable determining when to stop or start stimulation, is performed according to, or in cooperation with, known methods and devices for doing so. Some non-limiting examples of such devices and methods to recognize and detect the various features and patterns associated with respiratory effort and flow limitations include, but are not limited to: PCT Publication WO/2010/059839, titled A METHOD OF TREATING SLEEP APNEA, published on May 27, 2010; Christopherson U.S. Pat. No. 5,944,680, titled RESPIRATORY EFFORT DETECTION METHOD AND APPARATUS; and Testerman U.S. Pat. No. 5,522,862, titled METHOD AND APPARATUS FOR TREATING OBSTRUCTIVE SLEEP APNEA.

Moreover, in some examples various stimulation methods may be applied to treat obstructive sleep apnea, which include but are not limited to: Ni et al. WO 2013/023218, SYSTEM FOR SELECTING A STIMULATION PROTOCOL BASED ON SENSED RESPIRATORY EFFORT; Christopherson et al. U.S. Pat. No. 8,938,299, SYSTEM FOR TREATING SLEEP DISORDERED BREATHING, issued Jan. 20, 2015; and Wagner et al. WO 2016/149344, STIMULATION FOR TREATING SLEEP DISORDERED BREATHING, published Sep. 22, 2016, each of which is hereby incorporated by reference in its entirety.

Figure 8:
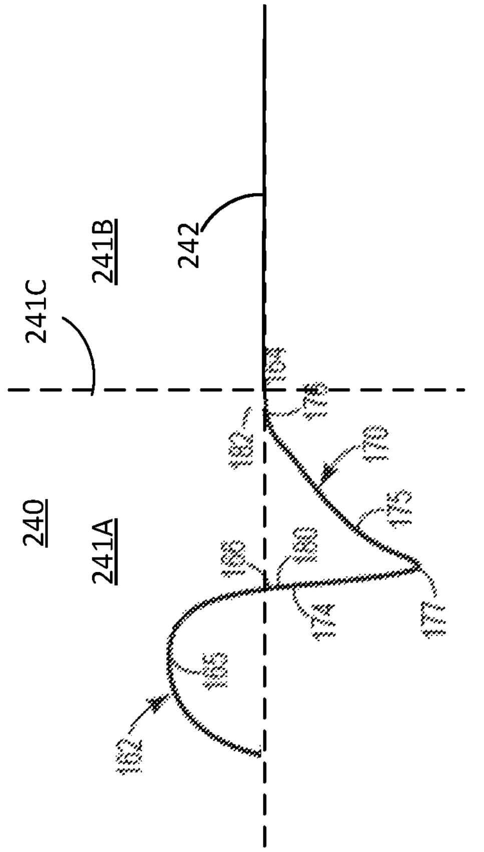
FIG. 8 is diagram schematically representing an example respiratory waveform including a normal respiratory cycle followed by a central sleep apnea event.

FIG. 8 is a diagram 240 illustrating a respiratory cycle of a normal breathing pattern 241A followed by an abnormal breathing pattern 241B, according to one example of the present disclosure. As shown in FIG. 8, disordered breathing pattern 241B reflects an absence of inspiration associated with a lack of respiratory drive, which may correspond to central sleep apnea. In the disordered breathing pattern 241B, a complete absence of inspiration is exhibited as represented by the flat solid line 242.

Figure 9:
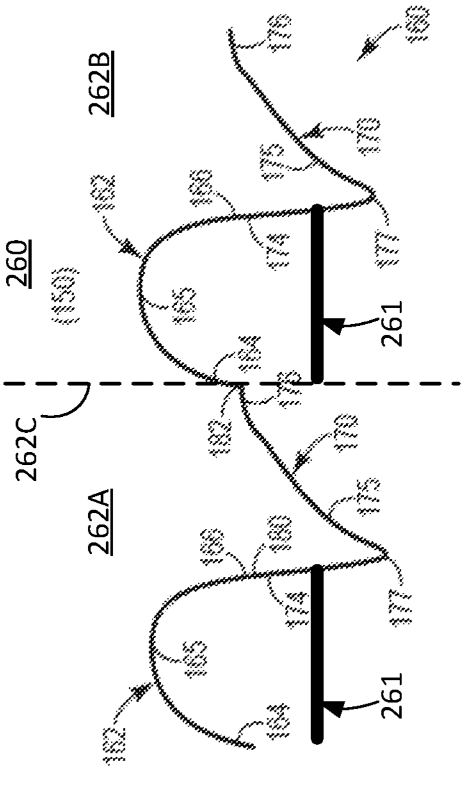
FIG. 9 is diagram schematically representing an example respiratory waveform including stimulation performed during each inspiratory phase of the respiratory cycle.

However, as shown in FIG. 9, via application of stimulation (as represented via solid bars 261) to a central sleep apnea-related nerve (e.g. 146 in FIG. 6) during at least a portion of an inspiratory phase 162 of the respiratory cycles 262A, 262B, a more regular or completely normal inspiratory phase may be restored, thereby treating central sleep apnea and/or preventing future episodes of central sleep apnea.

With these sample respiratory patterns in mind and the examples of at least FIGS. 1-6, further example implementations of methods and/or devices of sleep disordered breathing (SDB) care will be described.

For instance, with regard to at least the methods and/or devices of treating multiple type sleep apnea as previously described in association with at least FIGS. 1-9, FIG. 10 provides a flow diagram which schematically represents at 320 a portion of a method like method 30 (FIG. 3) or 50 (FIG. 5A). In particular, this example method may comprise synchronizing the stimulation of the upper airway patency-related first nerve (e.g. 14 in FIG. 1; 30 in FIGS. 3, 5A) relative to at least an inspiratory phase of a respiratory cycle, as was previously illustrated for inspiratory phase 202B in FIG. 7B.

In some such examples of the method shown at 320 in FIG. 10, synchronization means delivering the stimulation in a manner which at least partially overlaps with an inspiratory phase of a respiratory cycle, such as but not limited to the overlap of stimulation 221 of an upper airway patency-related nerve in FIG. 7B which overlaps with the inspiratory phase 202B, as shown in FIG. 7B.

In some such examples, the stimulation 221 (FIG. 7B) may overlap with a substantial majority of the inspiratory cycle. The term "substantial majority" comprises at least 50 percent in some examples, at least 60 percent in some examples, at least 70 percent in some examples, at least 80 percent in some examples, at least 90 percent in some examples, or at least 95 percent in some examples. In the particular example shown in FIG. 7B, the stimulation completely overlaps with or nearly completely overlaps with the duration of the inspiratory phase 202B of the respiratory cycle.

In some examples of "synchronization", the stimulation relative to the inspiratory phase may extend to a pre-inspiratory period and/or a post-inspiratory phase. For instance, in some such examples, a beginning of the synchronization may occur at a point in each respiratory cycle which is just prior to an onset of the inspiratory phase. In some examples, this point may be about 200 milliseconds, or 300 milliseconds prior to an onset of the inspiratory phase.

In some examples in which the stimulation is synchronous with at least a portion of the inspiratory phase, the upper airway muscles are contracted via the stimulation to ensure they are open at the time the respiratory drive controlled by the central nervous system (e.g. 140 in FIG. 6) initiates an inspiration (inhalation). In some such examples, in combination with the stimulation occurring during the inspiratory phase, example implementation of the above-noted pre-inspiratory stimulation helps to ensure that the upper airway is open before the negative pressure of inspiration within the respiratory system is applied via the diaphragm (e.g. 141 of FIG. 6) of the patient's body. In one aspect, this example arrangement may minimize the chance of constriction or collapse of the upper airway, which might otherwise occur if flow of the upper airway flow were too limited prior to the full force of inspiration occurring.

In some such examples, the stimulation of the upper airway patency-related nerve may be synchronized to occur with at least a portion of the expiratory period.

With regard to at least the methods of treating sleep apnea as previously described in association with at least FIGS. 1-9, in some examples as shown at 325 in FIG. 11 at least some such methods may comprise performing the delivery of stimulation to the upper airway patency-related first nerve without synchronizing such stimulation relative to a portion of a respiratory cycle.

In some examples, the term "without synchronizing" may refer to performing the stimulation independently of timing of a respiratory cycle. In some examples, the term "without synchronizing" may refer to performing the stimulation being aware of respiratory information but without necessarily triggering the initiation of stimulation relative to a specific portion of a respiratory cycle or without causing the stimulation to coincide with a specific portion (e.g. inspiratory phase) of respiratory cycle.

In some examples, in this context the term "without synchronizing" may refer to performing stimulation upon the detection of sleep disordered breathing (e.g. obstructive sleep apnea events) but without necessarily triggering the initiation of stimulation relative to a specific portion of a respiratory cycle or without causing the stimulation to coincide with the inspiratory phase. At least some such examples may be described in Wagner et al. WO 2016/149344, STIMULATION FOR TREATING SLEEP DISORDERED BREATHING, published Sep. 22, 2016, and which is hereby incorporated by reference in its entirety.

In some examples, with regard to at least the methods and/or devices of treating multiple type sleep apnea as previously described in association with at least FIGS. 1-11, respiratory information about the inspiratory phase and other features of the respiratory cycle of a patient are obtained. Accordingly, as shown at 330 in FIG. 12, in some such examples, an example method comprises sensing respiratory information via a sensor. In some examples, the respiratory information includes at least inspiratory phase information. In some such examples the sensed inspiratory phase comprises a natural inspiratory phase. The natural inspiratory phase also may sometimes be referred to as an intrinsic inspiratory phase.

However, in some such examples associated with at least FIG. 12, sensing the respiratory information may comprise sensing an artificial inspiratory phase induced by contraction of a diaphragm 141 innervated by the central sleep apnea-related nerve 146 (FIG. 5). In such examples it will be understood that the respiratory information being sensed, which may be used in synchronizing stimulation of the upper airway patency-related nerve, is at least partially produced via stimulation of a central sleep apnea-related nerve.

FIG. 13 is a diagram 335 schematically representing an example method. With regard to at least the methods of treating sleep apnea as previously described in association with at least FIGS. 1-6, in some examples as shown at 335 in FIG. 13 the example method may comprise performing the delivering of stimulation to the upper airway patency-related nerve independent of detection of any obstructive sleep apnea events. For instance, in some such examples the stimulation may delivered without attempting to detect obstructive sleep apnea events, behavior, while in some such examples, the stimulation may be delivered regardless of whether obstructive sleep apnea events are detected or not detected.

In one aspect, this method may sometimes be referred to as being at least one aspect or type of open loop stimulation. In some such examples, the implementation of stimulating an upper airway patency-related nerve (to treat at least obstructive sleep apnea) may be simplified because at least some elements to sense respiratory information may be omitted, because the amount of processing sensed respiratory information may be decreased, or the like.

FIG. 14 is a diagram 340 schematically representing an example method which performs stimulation to treat sleep apneas, such as at least obstructive sleep apnea and central sleep apnea, as described in association throughout the various examples of the present disclosure and in which the delivery of stimulation to an upper airway patency-related nerve may be performed without regard to classification of apnea type. In particular, in some such examples, the delivery of stimulation to the upper airway patency-related nerve does not first depend on attempting to detect or to classify breathing behavior of the patient as obstructive sleep apnea. Likewise, in some such examples the delivery of stimulation of a central sleep apnea-related nerve does not first depend on attempting to detect or to classify breathing behavior of the patient as central sleep apnea, as not being obstructive sleep apnea, as not being Cheyne-Stokes respiration, etc.

Moreover, as shown at 345 in FIG. 15, the method in FIG. 14 sometimes may further comprise performing the delivery of stimulation to the upper airway patency-related nerve (e.g. 14 in FIG. 1; 30 in FIGS. 3, 5A) without classifying detected sleep apnea behavior as at least one of a mixed sleep apnea event and a primarily OSA event. In the some such examples, the mixed sleep apnea event may be understood to be a combination of central sleep apnea (CSA) and obstructive sleep apnea (OSA) or some other combination of different sleep disordered breathing behaviors. In one aspect, this method may simplify implementing sleep disordered breathing (SDB) care because it may simplify sensing, processing, decision-making, and/or the like prior to implementing therapeutic stimulation.

FIG. 16 is a diagram 350 which schematically represents an example method like the method 340 in FIG. 14, except further comprising performing the delivery of stimulation to the central sleep apnea-related nerve (e.g. 24 in FIG. 2; 35 in FIGS. 4, 5A) without classifying detected sleep apnea behavior as at least one of a mixed sleep apnea event and a primarily central sleep apnea (CSA) event. In the some such examples, the mixed sleep apnea event may be understood to be a combination of central sleep apnea (CSA) and obstructive sleep apnea (OSA) or some other combination of different sleep disordered breathing behaviors. In one aspect, this method may simplify implementing sleep disordered breathing (SDB) care because it may simplify sensing, processing, decision-making, and/or the like prior to implementing therapeutic stimulation.

FIG. 17 is a diagram 355 which schematically represents an example method, which may further comprise at least one of the previously described example methods (e.g. at least 50 in FIG. 5A), and further comprising performing delivery of stimulation to the central sleep apnea-related nerve (e.g. 22 in FIG. 2) simultaneous with delivery of stimulation to the upper airway patency-related nerve (e.g. 14 in FIG. 1). In some such examples, this method may comprise performing both types of stimulation synchronous (or substantially synchronous) with an inspiratory phase of a respiratory cycle. In some such examples, however, while the stimulation of the central sleep apnea-related nerve may occur simultaneous with the stimulation of the upper airway patency-related nerve it does not mean that the stimulation of the central sleep apnea-related nerve occurs every time that the stimulation of the upper airway patency-related nerve occurs. Rather, because in at least some examples the stimulation of the central sleep apnea-related nerve is delivered solely upon detection of certain events, such as a lack of respiratory drive or effort, then the stimulation of central sleep apnea-related need not be performed every time stimulation of the upper airway patency-related nerve is performed. Nevertheless, per method 355, in some examples on occasions in which the stimulation of the central sleep apnea-related nerve is performed, then it will be delivered simultaneous with stimulation of the upper airway patency-related nerve (e.g. 14 in FIG. 1, 130 in FIG. 6).

FIG. 18A is a diagram 360 which schematically represents an example method, which may further comprise at least one of the previously described example methods (e.g. at least 35 in FIGS. 4, 5A, etc.), and further comprising performing delivery of stimulation to the central sleep apnea-related nerve (e.g. 22 in FIG. 2; 146 in FIG. 6) during at least one of: the inspiratory phase (e.g. FIG. 9); and during both the inspiratory phase and the expiratory phase of at least one respiratory cycle. In one aspect, at least some aspects of the example method of FIG. 18 have been described in association with at least FIGS. 8-9.

FIG. 18B is a diagram 365 which schematically represents an example method, which may further comprise at least one of the previously described example methods of stimulation in which the delivery of stimulation of the central sleep apnea-related nerve is performed without identifying a mid-breath point of a respiratory cycle.

FIG. 19 is a diagram 368 schematically representing an example method comprising at least some of substantially the same features and attributes as the previously described example methods (e.g. FIGS. 4, 5A, etc.) involving stimulation of at least the central sleep apnea-related nerve (e.g. 22 in FIG. 2; 146 in FIG. 6), while further comprising maintaining the delivery of stimulation of the central sleep apnea-related nerve in at least one of: at least a predetermined number of respiratory cycles; and through the end of the treatment period. The predetermined number of respiratory cycles may correspond to a number of respiratory cycles selected for a particular patient, or patients in general, which has been determined to alleviate central sleep apnea. Meanwhile, maintaining the delivery of stimulation of the central sleep apnea-related nerve through the end of the treatment period may be implemented in situations when it has been determined that the particular patient may exhibit further central sleep apnea if the stimulation were not maintained or when it is desired generally to ensure no further central sleep apnea events occur during the treatment period.

FIG. 20 is a diagram 370 schematically representing an example method comprising at least some of substantially the same features and attributes as the previously described example methods (e.g. FIGS. 4, 5A, etc.) involving stimulation of at least the central sleep apnea-related nerve (e.g. 22 in FIG. 2; 146 in FIG. 6), while further comprising delivering the stimulation at a suprathreshold intensity of stimulation (versus a subthreshold intensity level). In some such examples, the term "suprathreshold" comprises the scope and/or meaning as previously described in association with at least FIGS. 1-5B and in which the suprathreshold intensity level comprises contraction of the innervated muscles (e.g. diaphragm).

FIG. 21 is a diagram 373 schematically representing an example method comprising at least some of substantially the same features and attributes as the previously described example methods (e.g. FIGS. 4, 5A, etc.) involving stimulation of at least the central sleep apnea-related nerve (e.g. 22 in FIG. 2; 146 in FIG. 6), while further comprising performing the delivery of stimulation without holding a breath of a patient.

FIG. 22 is a diagram 375 schematically representing an example method comprising at least some of substantially the same features and attributes as the previously described example methods (e.g. 35 in FIGS. 4, 5A, etc.) involving stimulation of at least the central sleep apnea-related nerve (e.g. 22 in FIG. 2; 146 in FIG. 6), while further comprising detecting the central sleep apnea behavior via at least one of identifying a respiratory amplitude (during an inspiratory phase) of zero (or near zero) and identifying the respiratory amplitude as less than a threshold. In some such examples, the threshold may correspond to a non-zero respiratory amplitude observed for a particular patient (or typical patient) which is associated with a lack of respiratory effort for which stimulation of the central sleep apnea-related nerve may provide a therapeutic respiratory benefit in relation solely to central sleep apnea and/or in relation to both central sleep apnea and obstructive sleep apnea.

FIG. 23A is a diagram 380 schematically representing an example method comprising at least some of substantially the same features and attributes as the previously described example methods (e.g. 35 in FIGS. 4, 5A, etc.) involving stimulation of at least the central sleep apnea-related nerve (e.g. 22 in FIG. 2; 146 in FIG. 6), while further comprising, in the temporary absence of the inspiratory phase due to a central sleep apnea event(s), delivering stimulation to an upper airway patency-related nerve via a first stimulation protocol without synchronization relative to an inspiratory phase of a respiratory cycle.

In some such examples, the method 380 (FIG. 23B) of delivering stimulation via the first stimulation protocol may further comprise, as shown at 385 in FIG. 23B, at least one of: delivering stimulation continuously for a selected period of time; and delivering stimulation according to a cyclic pattern mimicking an intrinsic respiratory cycle.

In some such examples, the selected period of time is a predetermined duration (e.g. 30 seconds), determined based on the number of central sleep apnea events detected within a treatment period, or other suitable criteria.

As further described later in various examples in association with at least FIGS. 30A-37, the sensor(s) used in the foregoing devices and/or methods may be implantable within the patient's body and/or external to the patient's body, which in turn may be a wearable sensor and/or a non-contact sensor. In some examples of sensing respiratory information, the sensor is positioned adjacent to or coupled to respiratory-related tissue, such as the lungs, lung-related tissue, the diaphragm, etc. In some such examples, such respiratory sensing may sometimes be referred to as direct respiratory sensing at least to the extent that the sensor is adjacent to or coupled directly to respiratory-related tissue.

In some examples, the sensor may comprises a pressure sensor, bio-impedance sensor, acoustic sensor, accelerometer, etc. Further details regarding such types, forms, and placement of sensors will be described later in association with at least FIGS. 32-37.

Figure 24:
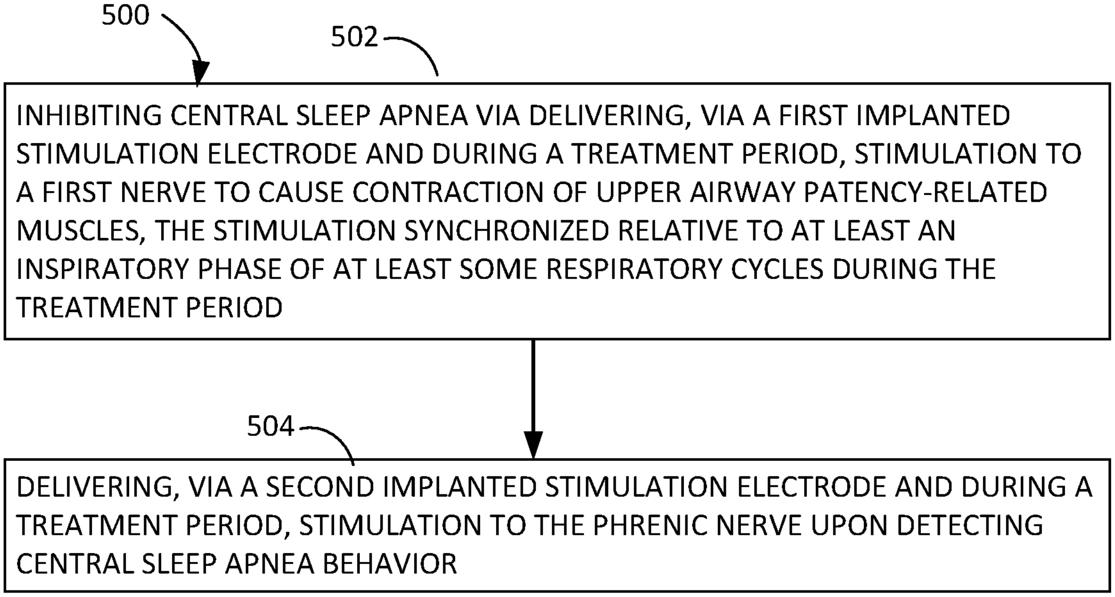
FIG. 24 is a flow diagram schematically representing an example method of treating multiple-type sleep apnea.

FIG. 24 is a flow diagram schematically representing an example method 500 of treating sleep apnea. As shown at 502 in FIG. 24, method 500 comprises inhibiting central sleep apnea via delivering, via a first implanted stimulation electrode and during a treatment period, stimulation to a first nerve (e.g. hypoglossal nerve) to cause contraction of upper airway patency-related muscles, the stimulation synchronized relative to at least an inspiratory phase of at least some respiratory cycles during the treatment period. As shown at 504 in FIG. 24, method 500 further comprises delivering, via a second implanted stimulation electrode and during a treatment period, stimulation to the phrenic nerve upon detecting central sleep apnea behavior.

Figure 25A:
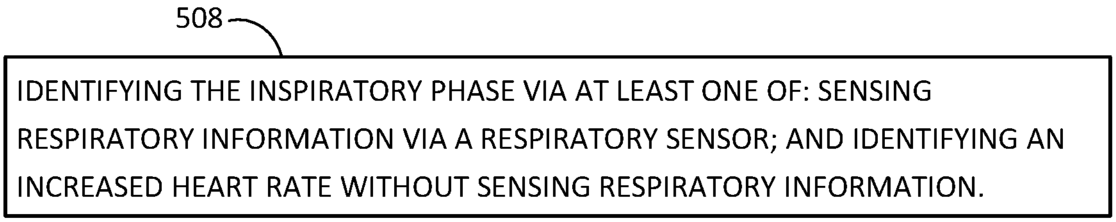
FIG. 25A is a diagram schematically representing an example method of treating sleep apnea, including identifying an inspiratory phase of a respiratory cycle.

With regard to at least the methods of treating sleep apnea as previously described in association with at least FIGS. 1-24, in some examples as shown at 508 in FIG. 25A such methods may comprise identifying the inspiratory phase via at least one of: sensing respiratory information via a respiratory sensor; and identifying an increased heart rate without sensing respiratory information.

Figure 25B:
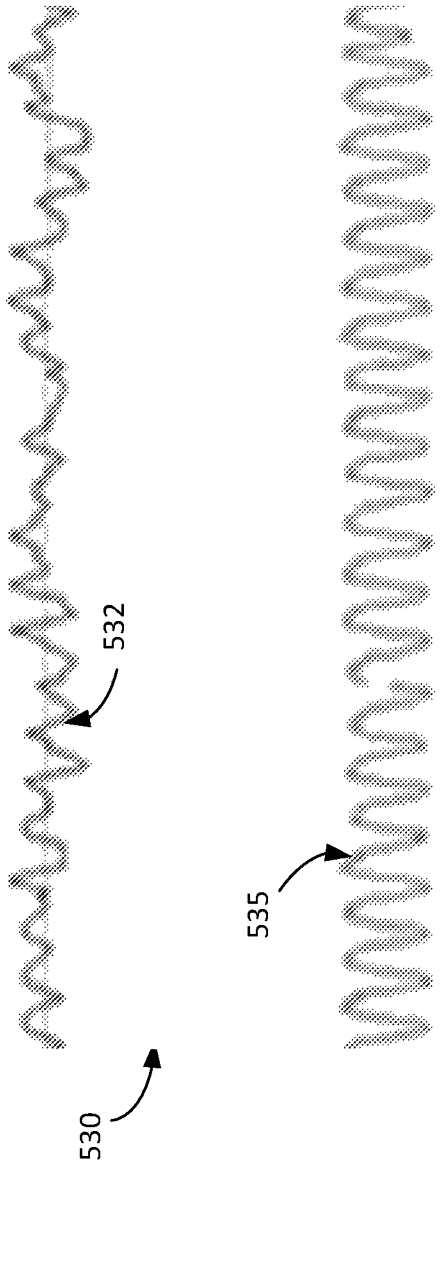
FIG. 25B is a diagram schematically representing an example heart rate waveform and an example respiratory effort waveform.

FIG. 25B is a diagram 530, which schematically represents a profile of heart rate 532 juxtaposed relative to a profile of respiratory effort 535 (e.g. chest motion) and which generally demonstrates a correlation between heart rate 532 and respiratory effort 535 such that at least some aspects of heart rate 532 may be used instead of respiratory sensing to determine, at least, an inspiratory phase of a respiratory cycle. In some such examples, an increased heart rate may be indicative of an inspiratory phase.

In some such examples, the method may comprise identifying increased heart rate per a heart rate variability (HRV) signal, which may comprise a Respiratory Sinus Arrhythmia (RSA) signal. In some examples, the heart rate variability (HRV) signal can be derived from electrocardiogram (ECG) signals, which may in turn be obtained from implanted leads within the body (e.g. a lead extending to the IPG case) or from an accelerometer signal, as further described later in association with at least FIGS. 32-37. In some such examples, the HRV signal may be determined via a ballistocardiogram/seismocardiogram, as further described later in association with at least FIG. 34A. In one aspect, the variability in heart rate that typically occurs with each breathing cycle is termed Respiratory Sinus Arrhythmia (RSA), where heart rate increases during inspiration and decreases during expiration.

With this in mind, during central apnea events where no respiratory effort is present, RSA is reduced or is absent. Therefore, heart rate can be used to determine inspiratory periods and to determine if an apnea event is central in nature. In some examples, this information may be employed when it is infeasible to determine, via the respiratory sensor signal, whether the lack of respiration is due to lack of effort or airway obstruction. In some cases, both respiratory sensor signals and HR signals are used in tandem to increase reliability of inspiration detection and/or detection of central and/or obstructive sleep apneas.

Figure 25C:
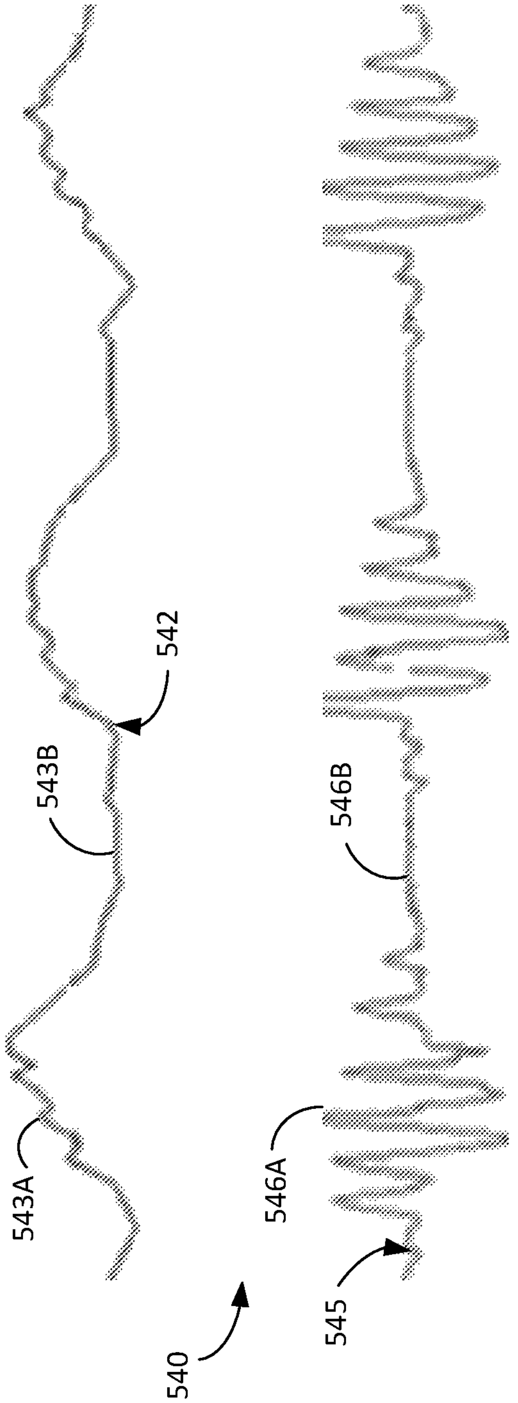
FIG. 25C is a diagram schematically representing an example cyclic variation heart rate waveform.

FIG. 25C is a diagram 540 schematically representing cyclic variation in heart rate (CVHR) 542, which provides one example of a heart rate variability (HRV) signal. As noted above, one form of heart rate variability may comprise respiratory sinus arrhythmia (RSA), which may be used to indicate the presence of central sleep apnea behavior in some examples. In FIG. 25C, the profile cyclic variation in heart rate (CVHR) 542 is juxtaposed relative to a profile of respiratory effort (e.g. chest motion) 545. Among other features revealed via diagram 540, in one aspect the CVHR profile 542 may include periods of respiratory sinus arrhythmia (RSA) (e.g. 534A) and absence of RSA (at 543B). As further shown in diagram 540 of FIG. 25C, in some examples the respiratory effort profile 545 may reveal absences of respiratory effort (e.g. 546B) in between periods of respiratory effort (e.g. 546A), with these absences of respiratory effort being indicative of central sleep apnea behavior, in some examples. As shown via the juxtaposition of profiles 542, 545 in FIG. 25C, the absence of RSA (e.g. 543B) in the CVHR profile 542 may be correlated with the absence (e.g. 546B) of respiratory effort in profile 545, such that the absence of RSA (or significant decrease in RSA) may be used as an indicator of central sleep apnea behavior (e.g. events).

As noted above and elsewhere throughout various examples of the present disclosure, information obtained via at least the example arrangement in FIGS. 25B, 25C may be used to detect central sleep apnea behavior in the absence of a respiratory signal/information and/or may be used to identify increased heart rate for indication of an inspiratory phase. Accordingly, via at least some example methods of the present disclosure, central sleep apnea behavior and/or inspiratory phase, as detected via heart rate information as described above, may be used as a trigger to stimulate a central sleep apnea-related nerve (e.g. phrenic nerve) and/or to synchronize the stimulation of the central sleep apnea-related nerve.

At least some such example methods are described and illustrated below in association with at least FIGS. 26-28B.

FIG. 26 is a flow diagram schematically representing an example method 550 of treating sleep apnea. In some examples, method 550 comprises at least some of substantially the same features and attributes as the examples previously described in association with at least FIGS. 1-25C. As shown at 562 in FIG. 26, method 550 comprises determining at least an inspiratory phase of at least some respiratory cycles via sensing heart rate variability (HRV) information; As shown at 554 in FIG. 26, method 550 comprises delivering, via a first implanted stimulation electrode and during a treatment period, stimulation to the hypoglossal nerve to cause contraction of upper airway patency-related muscles, the stimulation being synchronized relative to the determined inspiratory phase throughout the treatment period. As shown at 556 in FIG. 26, method 550 comprises delivering, via a second implanted stimulation electrode and during the treatment period, stimulation to the phrenic nerve upon detecting, via the sensed HRV information, a heart rate variability (HRV) of substantially zero. It will be understood that when the heart rate variability is zero or substantially zero, then the heart rate is substantially constant.

In some examples, as shown at 570 in FIG. 27A, method 550 may further comprise performing the determining the inspiratory phase (among other portions of a respiratory cycle) includes sensing respiratory information, such as via using a respiratory sensor or in some examples a respiratory-related sensor.

In some examples, as shown at 572 in FIG. 27B, method 550 may further comprise performing the determining the inspiratory phase without sensing respiratory information. In some such examples, the method may further comprise sensing the respiratory information without using a respiratory sensor. Accordingly, in some such examples, as shown at 575 in FIG. 28A the method (based on method 550) may comprise sensing the heart rate variability information without using a respiratory sensor, such as via sensing respiratory sinus arrhythmia (RSA) information. The detecting may comprise detecting the heart rate variability as an absence of respiratory sinus arrhythmia or as a substantial decrease in respiratory sinus arrhythmia. In some such examples, as shown at 580 in FIG. 28B the method 550 may further comprise performing the delivery of stimulation to the phrenic nerve upon the detected the absence of respiratory sinus arrhythmia or the substantial decrease in respiratory sinus arrhythmia.

Figure 29:
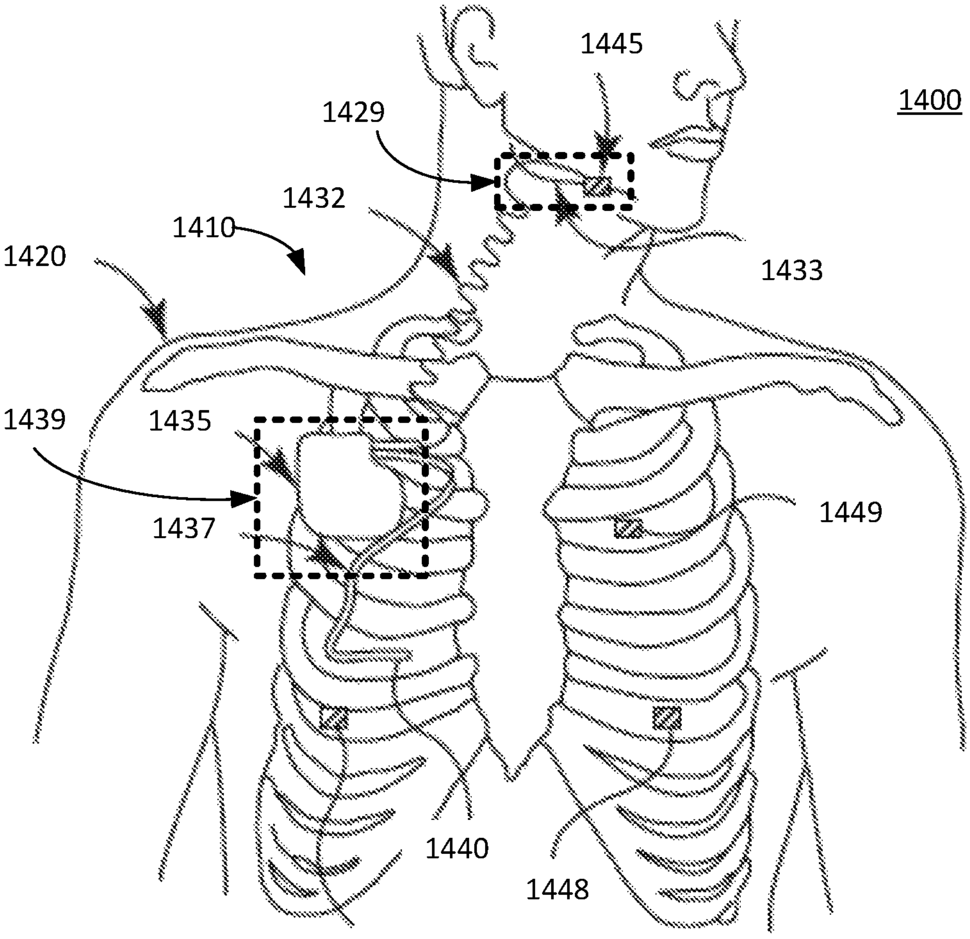
FIG. 29 is a diagram schematically representing an example stimulation device for treating sleep apnea, which includes a pulse generator and a sensor.

FIG. 29 is a diagram 1400 schematically representing a patient's body 1420 and an example stimulation device 1410. In some examples, the device 1410 may comprise one example implementation of the device 10 shown in FIG. 1 and/or may comprise at least some of substantially the same features and attributes of the various example devices described throughout the present disclosure. In more general terms, in some examples the device 1410 may be used to implement any of the example methods described herein which comprise a method of stimulating an upper airway patency-related nerve to treat obstructive sleep apnea, with or without an associated stimulation of a central sleep apnea-related nerve to treat central sleep apnea.

As shown in FIG. 29, device 1410 comprises an implantable pulse generator (IPG) 1435 positionable within the patient's body 1420. In some examples, the IPG 1435 is implanted within a pectoral region. The device 1410 also comprises a stimulation lead 1432 which is electrically coupled with, and extends from, the IPG 1435. The lead 1432 includes a stimulation electrode portion 1445 and extends from the IPG 1435 so that the stimulation electrode 1445 is positioned in contact with an upper airway patency-related nerve 1433 (e.g. hypoglossal nerve) to enable delivery of stimulation. An exemplary implantable stimulation system in which lead 1432 may be utilized, for example, is described in U.S. Pat. No. 6,572,543 to Christopherson et al., and which is incorporated herein by reference in its entirety. In some examples, the stimulation electrode 1445 may comprise at least some of substantially the same features and attributes as described in Bonde et al. U.S. Pat. No. 8,340,785, SELF EXPANDING ELECTRODE CUFF, issued on Dec. 25, 2102 and Bonde et al. U.S. Pat. No. 9,227,053 SELF EXPANDING ELECTRODE CUFF, issued on Jan. 5, 2016, both which are hereby incorporated by reference in their entirety.

In some examples, the electrode 1445 also may sometimes be used as part of a sensing arrangement, such as one but not limited to the multi-sensor impedance sensing arrangements further described below.

In some examples, device 1410 comprises at least one sensor 1440 which is electrically coupled to the IPG 1435 and extends from the IPG 1435 via lead 1437, which may sense at least respiratory information. It will be understood that sensor 1440 may embodied in different forms and for sensing other types of information, as described elsewhere in various examples of the present disclosure, such as but not limited to FIGS. 32-37.

In some example, the sensor 1440 detects respiratory effort including respiratory patterns (e.g., inspiration, expiration, respiratory pause, etc.). In some such examples, this respiratory information may be used to trigger activation of an electrode portion 1445 to stimulate a target nerve, may be used to detect sleep apneas (e.g. obstructive, central, etc.), etc. In some such examples, via this arrangement, the IPG 1435 receives sensor waveforms from the respiratory sensor 1440, thereby enabling the IPG 1435 to deliver electrical stimulation, which in some examples may be synchronous with inspiration (or synchronized relative to another aspect of the respiratory cycle).

In some examples, sensing to detect at least respiratory information and/or other physiologic information (as described throughout at least some examples of the present disclosure) may be implemented and performed via an accelerometer, such as but not limited to the examples described below in association with at least FIGS. 32-37. In some such examples, an accelerometer may be housed within or incorporated in a pulse generator (e.g. 1435) while in some examples, the accelerometer may form part of a lead body, end of a lead, etc.

In some examples, the sensor 1440 comprises a pressure sensor, which may sense respiratory pressure.

In some examples, the sensor 1440 may comprise a bio-impedance sensor or pair of bio-impedance sensors and can be located in regions other than the pectoral region. In one aspect, such an impedance sensor is configured to sense a bio-impedance signal or pattern whereby the control unit evaluates respiratory patterns within the bio-impedance signal. For bio-impedance sensing, in some examples, electric current will be injected through an electrode portion within the body and an electrically conductive portion of a case of the IPG 1435 with the voltage being sensed between two spaced apart stimulation electrode portions (or also between one of the stimulation electrode portions and the electrically conductive portion of the case of IPG 1435) to compute the impedance.

In some examples, device 1410 may comprise sensors to further obtain physiologic data associated with respiratory functions. For example, device 1410 may comprise various sensors (e.g., sensors 1447, 1448, 1449 in FIG. 30) distributed about the chest area for measuring a trans-thoracic bio-impedance signal, other respiratory-associated signals, or an electrocardiogram (ECG).

In some examples, such as when a method or device is to operate without sensing respiratory information or without sensing via a respiratory sensor, then at least some examples of device 1410 of FIG. 29 may omit sensors 1447, 1448, 1449 and/or 1440 or device 1410 may selectively not utilize such sensors.

In some examples, device 1410 is totally implantable. However, in some examples, one or more components of the device 1410 are not implanted in a body of the patient. A few non-limiting examples of such non-implanted components include external sensors (respiration, impedance, etc.), an external processing unit, or an external power source. Of course, it is further understood that the implanted portion(s) of the system provides a communication pathway to enable transmission of data and/or controls signals both to and from the implanted portions of the system relative to the external portions of the system. The communication pathway may comprise a radiofrequency (RF) telemetry link or other wireless communication protocols.

Figure 30A:
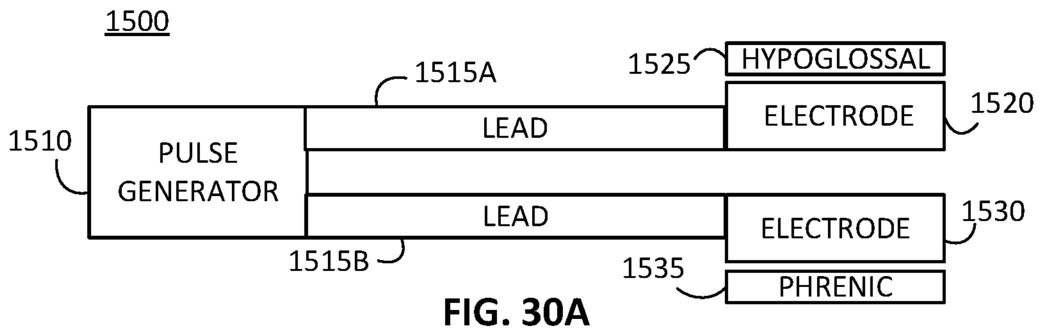
FIG. 30A is a diagram schematically representing an example stimulation device including two leads to stimulate an upper airway patency-related nerve and a central sleep apnea-related nerve.
Figure 30B:
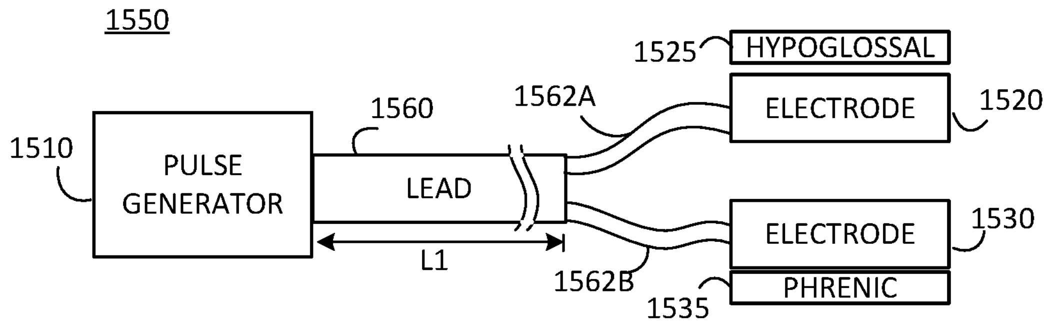
FIG. 30B is a diagram schematically representing an example stimulation device including a proximal common lead and two distal leads to stimulate an upper airway patency-related nerve and a central sleep apnea-related nerve.
Figure 30C:
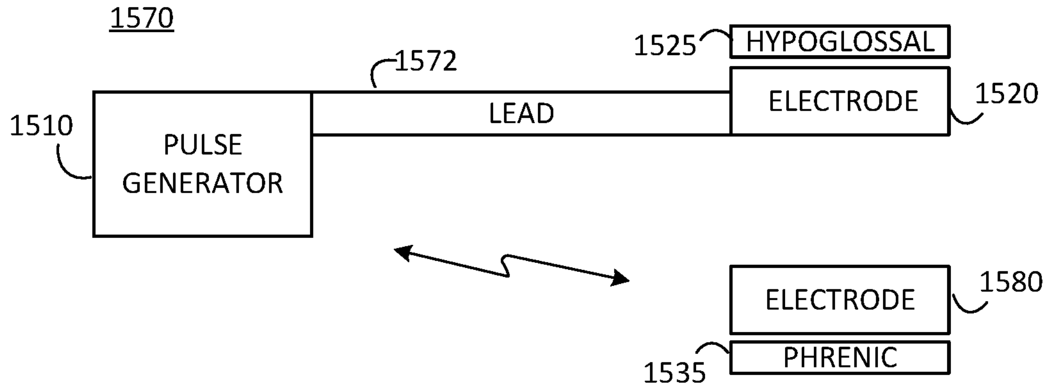
FIG. 30C is a diagram schematically representing an example stimulation device including a lead to stimulate an upper airway patency-related nerve and a freestanding electrode to stimulate central sleep apnea-related nerve.
Figure 30D:
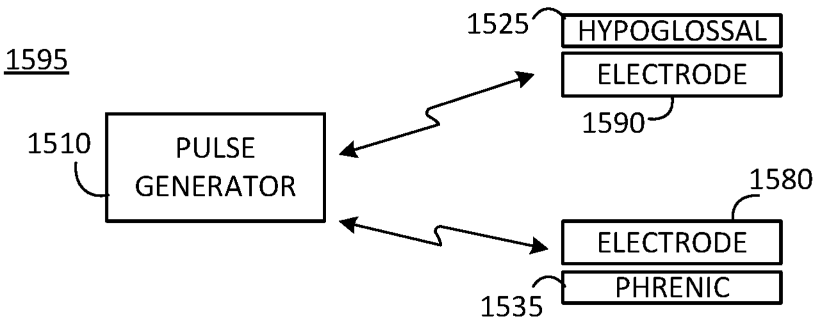
FIG. 30D is a diagram schematically representing an example stimulation device including a freestanding electrode to stimulate an upper airway patency-related nerve and a freestanding electrode to stimulate central sleep apnea-related nerve.
Figure 30E:
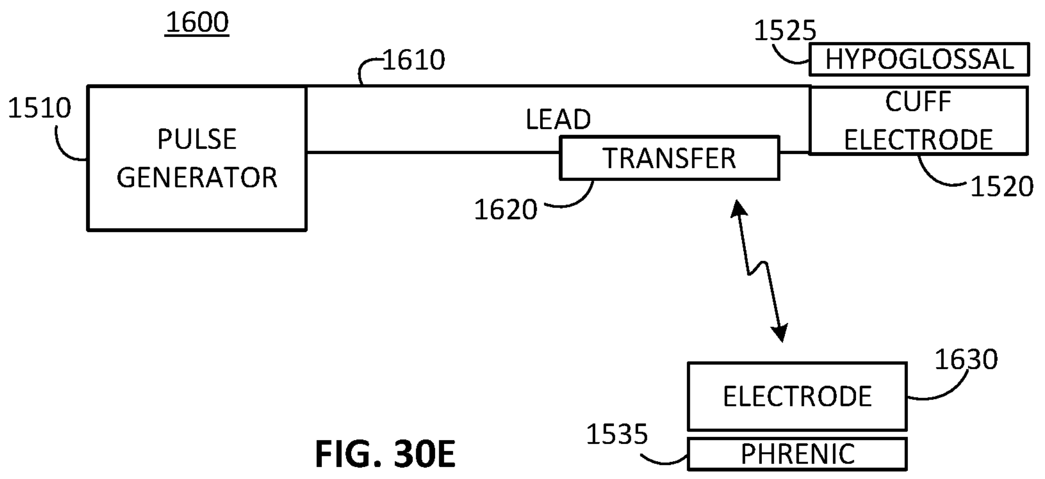
FIG. 30E is a diagram schematically representing an example stimulation device including a lead to stimulate an upper airway patency-related nerve with a transfer element and a freestanding electrode to stimulate central sleep apnea-related nerve.
Figure 30F:
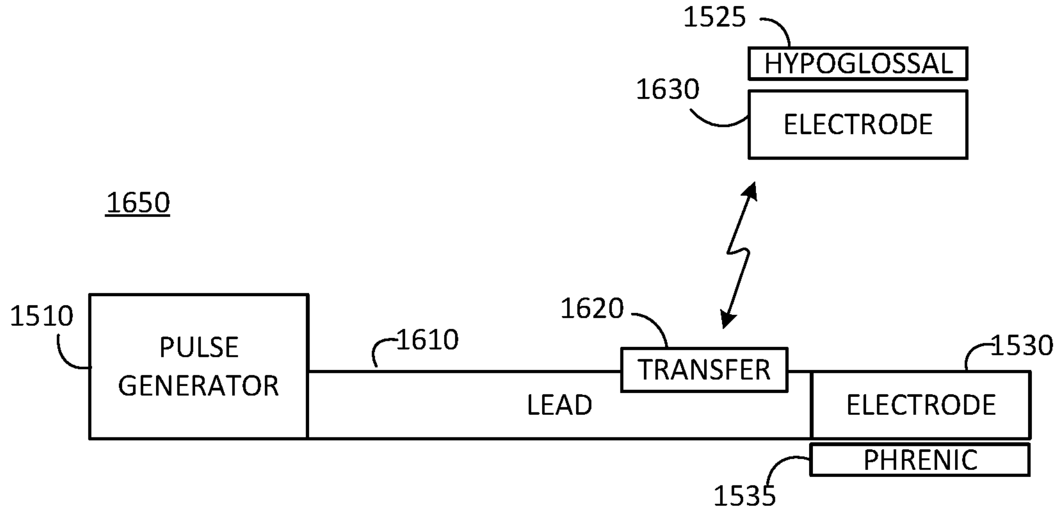
FIG. 30F is a diagram schematically representing an example stimulation device including a lead to stimulate an central sleep apnea-related nerve with a transfer element and a freestanding electrode to stimulate an upper airway patency-related nerve.
Figure 30G:
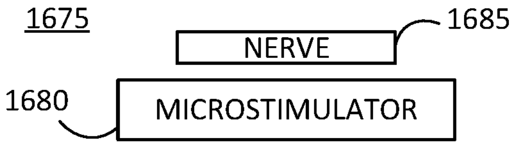
FIG. 30G is a diagram schematically representing an example stimulation device including a microstimulator to stimulate a sleep apnea-related nerve.
Figure 30H:
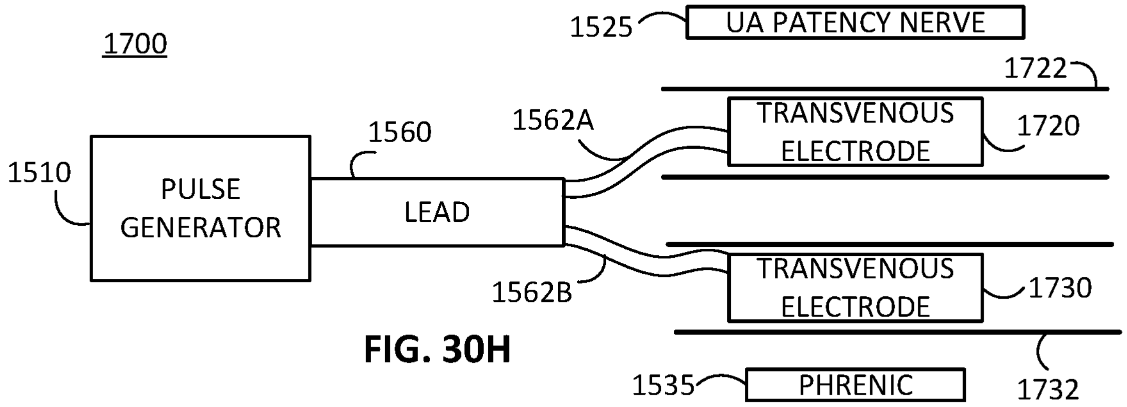
FIG. 30H is a diagram schematically representing an example stimulation device including a proximal common lead and two distal leads placed transvenously to stimulate an upper airway patency-related nerve and a central sleep apnea-related nerve.
Figure 30I:
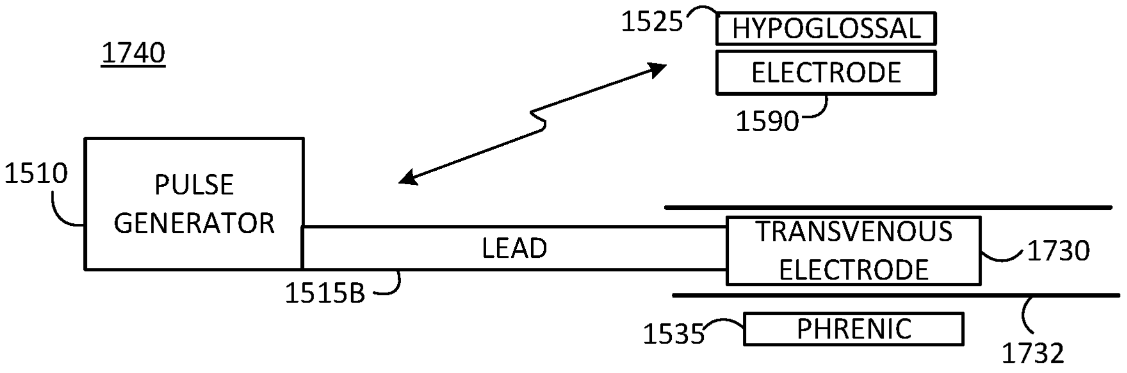
FIG. 30I is a diagram schematically representing an example stimulation device including one lead placed transvenously to stimulate a phrenic nerve and a freestanding electrode to stimulate the hypoglossal nerve.
Figure 30J:
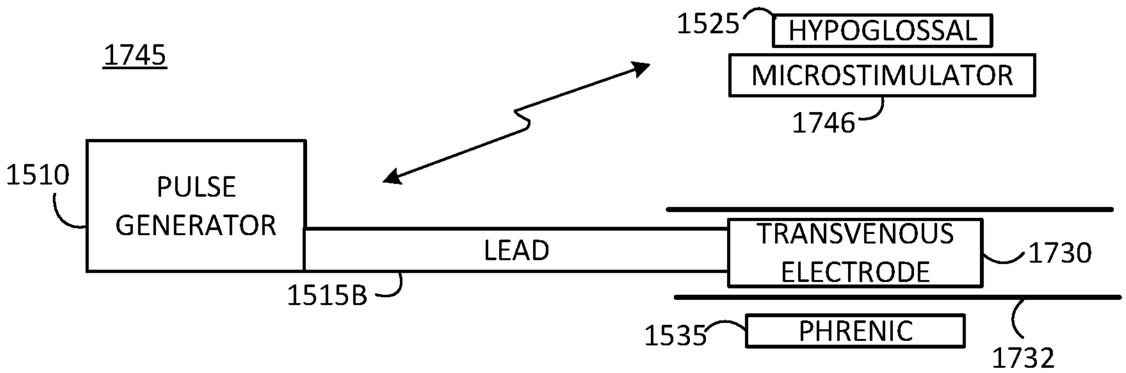
FIG. 30J is a diagram schematically representing an example stimulation device including one lead placed transvenously to stimulate a phrenic nerve and a freestanding microstimulator to stimulate the hypoglossal nerve.
Figure 30K:
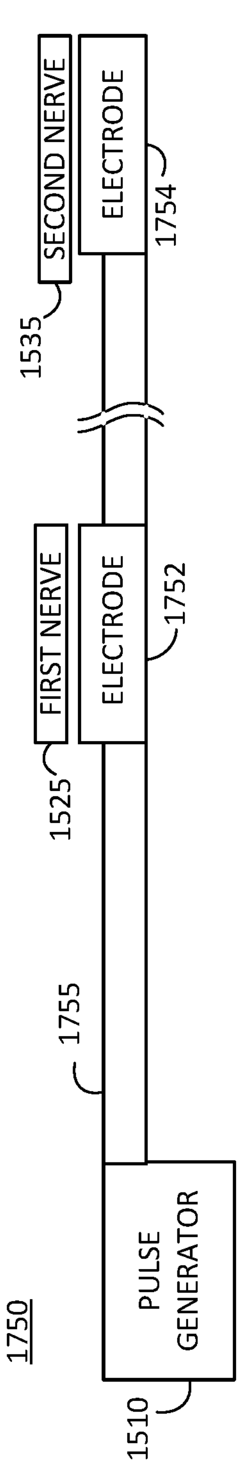
FIG. 30K is a diagram schematically representing an example stimulation device including a single lead with a proximal, first electrode to stimulate a first nerve and a distal, second electrode to stimulate a second nerve.
Figure 31:
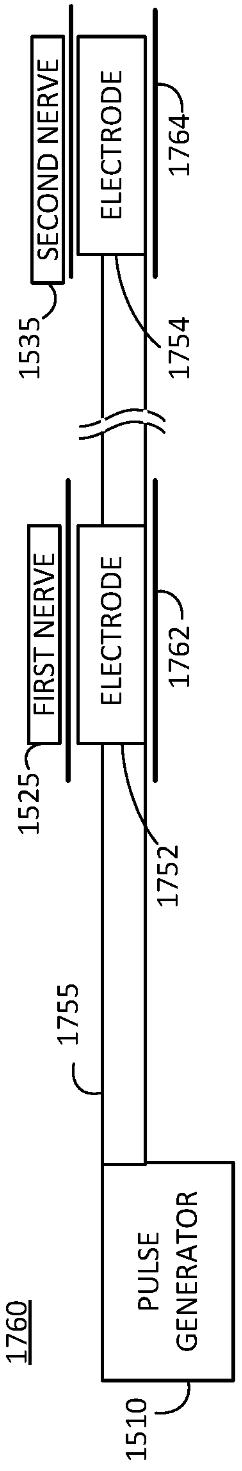
FIG. 31 is a diagram schematically representing an example stimulation device including a single lead with a portion placed within the vasculature and having a proximal, first electrode to stimulate a first nerve and a distal, second electrode to stimulate a second nerve.

FIGS. 30A-31 schematically represent examples including various electrodes, leads, etc., which may comprise example implementations of the devices and/or methods previously described in association with FIGS. 1-29, 32-37, and/or 38A-38C.

FIG. 30A is a diagram schematically representing an example device 1500 to stimulate an upper airway patency-related nerve and a central sleep apnea-related nerve. In some examples, the device 1500 comprises at least some of substantially the same features and attributes as device 1410, except further comprising a second stimulation lead 1515B and electrode 1530 for stimulating a central sleep apnea-related nerve, such as the phrenic nerve 1535. As shown in FIG. 30A, the second stimulation lead 15158 is electrically coupled to, and extends from, an implantable pulse generator (IPG) 1510, which may comprise at least some of substantially the same features and attributes as IPG 1435 in FIG. 29. The second stimulation lead 15158 is separate from, and independent from, a first stimulation lead 1515A supporting an electrode 1520 for at least electrically coupling relative to an upper airway patency-related nerve, such as the hypoglossal nerve 1525. In some examples, the stimulation leads 1515A, 15158 comprises at least some of substantially the same features as lead 1432 in FIG. 29. In some examples, the electrodes 1520 and/or 1530 may comprise at least some of substantially the same features and attributes as the electrode 1445 in FIG. 29.

In some examples, lead 1515A with cuff electrode 1520 and lead 15158 with electrode 1530 are implanted subcutaneously with each electrode 1520, 1530 being implanted relative to the respective nerves 1525, 1535, and then their leads tunneled back to the pulse generator 1510. However, in some examples, the electrode 1530 for the phrenic nerve 1535 may be implanted laparoscopically or via other methods.

In some examples, both of the electrodes 1520, 1530 are implanted in a neck region (e.g. 124 in FIG. 6) of the patient's body via a subcutaneous or percutaneous access procedure which is external of the patient's vasculature.

In some examples, one or both of electrodes 1520, 1530 may comprise cuff electrodes while in some examples, one or both electrodes 1520, 1530 may comprise electrodes other than cuff electrodes. In some examples, whether or not electrodes 1520, 1530 are cuff electrodes, one or both of electrodes 1520, 1530 may each comprise an array of electrodes, which may be arranged in a wide variety of configurations, such as but not limited to being arranged in a row, rows, in parallel, in a grid (e.g. 2×2, 3×3, etc.), and combinations thereof.

In general terms, the hypoglossal nerve may be accessible in the neck region and the phrenic nerve may be accessible in the neck and trunk regions. Via at least example device 1500, the hypoglossal nerve may be stimulated via a tunneled lead and cuff electrode at the neck, and the phrenic nerve may be stimulated via a tunneled lead and electrode at the neck. In this way, placement of stimulation electrodes at the hypoglossal and phrenic nerves at the neck may allow a minimum number of incisions and lead tunnels.

FIG. 30B is a diagram schematically representing an example device 1550 to stimulate an upper airway patency-related nerve and a central sleep apnea-related nerve. In some examples, device 1550 comprises at least some of substantially the same features and attributes as device 1500 in FIG. 30A, except comprising a bifurcated lead as shown in FIG. 30B. In particular, device 1550 comprises a single proximal lead portion 1560 electrically coupled to, and extending from, pulse generator 1510 and a pair of separate distal lead portions 1562A, 1562B extending distally from the single proximal lead portion 1560. One distal lead portion 1562A supports electrode 1520 while the other distal lead portion 1562B supports electrode 1530. The single proximal lead portion 1560 may sometimes be referred to as a common proximal lead portion. In some examples, the single proximal lead portion 1560 has a length L1 substantially greater than a length of either respective distal lead portion 1526A, 1526B. In some examples, the length of single proximal lead portion 1560 is at least 5×, 6×, 7×, 8×, etc. the length of either distal lead portion 1526A, 1526B.

In one aspect, this bifurcated distal lead arrangement may simplify implanting the device 1550 and improve its reliability. In particular, the single proximal lead portion 1560 enables use of a single tunnel from the incision (at which the cuff electrodes 1520, 1530 are implanted subcutaneously) to a pocket 1439 in the patient's body in which the pulse generator 1510 is to be implanted. Use of a single lead (e.g. single proximal lead portion 1560) and a corresponding single subcutaneous tunnel between an incision area (e.g. dashed lines 1429 in FIG. 29) in the neck region (e.g. 1425 in FIG. 29) and the generator pocket (e.g. dashed lines 1439 in FIG. 29) in the pectoral region may increase patient comfort. In addition, this arrangement also permits just a single lead connection to the pulse generator 1510 such that a connector block of the pulse generator 1510 may be smaller than if two stimulation leads were to be connected to the pulse generator 1510. This smaller profile pulse generator may further simplify implantation, increase patient comfort, etc.

Moreover, it may be understood that if one sought to use a device which comprises two separate leads (each having a cuff electrode) instead of the example single proximal lead portion 1560, the formation and use of a second tunnel after formation of a first tunnel (and placement of a first lead in the first tunnel) may compromise the first tunnel and/or first lead. Accordingly, via at least the example single proximal lead portion 1560, the example device 1550 may better preserve the integrity of a tunnel created between the incision area 1429 in the neck region and the incision area 1439 in the pectoral region while also simplifying the overall implantation procedure.

With regard to at least FIGS. 30A-30B, it will be understood that in some examples, the lead 1515B (FIG. 30A) or the lead 1526B (FIG. 30B) may be tunneled into a subcutaneous position at which the cuff electrode 1530 may engage the phrenic nerve for stimulating the phrenic nerve 1535.

FIG. 30C is a diagram schematically representing an example device 1570 to stimulate an upper airway patency-related nerve 1525 and a central sleep apnea-related nerve 1535. In some examples, device 1570 comprises at least some of substantially the same features and attributes as device 1500 in FIG. 30A, except comprising having just a single lead 1572 to support cuff electrode 1520 and a separate electrode 1580 in wireless communication with pulse generator 1510. The separate electrode 1580 may be implanted adjacent a nerve, and via the wireless communication, receive power and/or control signals from the pulse generator 1510. In some examples, as shown in FIG. 30C, the separate wireless electrode 1580 may be implanted adjacent a central sleep apnea-related nerve such as the phrenic nerve 1535. However, in some examples the separate wireless electrode 1580 may be implanted adjacent an upper airway patency-related nerve (e.g. hypoglossal), while the lead 1572 and electrode 1520 may be implanted for use in stimulating the phrenic nerve 1535. While the freestanding separate electrode 1580 may still involve an implantation, it would not involve tunneling and thereby may simplify and reduce the relative invasiveness of the overall procedure. Accordingly, device 1570 may enjoy at least some of substantially the same features and attributes as a single lead configuration, such as device 1560 in FIG. 30B.

FIG. 30D is a diagram schematically representing an example device 1595 in which a freestanding separate electrode 1590 is implanted to stimulate an upper airway patency-related nerve 1525 and the freestanding separate electrode 1580 (FIG. 30C) is implanted to stimulate central sleep apnea-related nerve 1535. In a manner at least similar to that previously described in association with FIG. 30C, each freestanding electrode 1580, 1590 may communicate wirelessly (for power and/or control signals) with the pulse generator 1510.

In some such examples, each electrode 1580, 1590 may comprise at least some features and attributes of a micro-stimulator, as further described later in association with at least FIG. 30G. In such examples, the pulse generator 1510 may be simplified to act as a single controller or control portion, power source, etc. without transmitting a stimulation signal to the respective micro-stimulator-based electrodes 1580, 1590. In this way, the simplified pulse generator 1510 may coordinate respective operation and stimulation via the respective electrodes 1580, 1590. In some such examples, one or both electrodes 1580, 1590 also may at least sometimes act as a sensing electrode to provide physiologic and/or therapy information to the simplified pulse generator 1510.

FIG. 30E is a diagram schematically representing an example device 1600 in which a lead 1610 (e.g. lead 1515A in FIG. 30A) supporting a cuff electrode 1520 is implanted to engage and stimulate an upper airway patency-related nerve 1525 and a freestanding separate electrode 1630 (e.g. 1590 in FIG. 30D) is implanted adjacent to, and to stimulate, a central sleep apnea-related nerve 1535. In addition, the lead 1610 may further comprise a transfer element 1620 to wirelessly transfer power and/or control signals (e.g. power, stimulation, and/or sensing) from the pulse generator 1510 to and from the freestanding separate electrode 1630. As in the prior examples, lead 1610 also communicate power, control signals, stimulation signals, and/or sensing signals between the pulse generator 1510 and the electrode 1520.

Via this arrangement, a reliable implantation route and procedure and reliable stimulation lead/elements may be used to stimulate the hypoglossal nerve or other upper airway patency-related nerve, while electrode 1630 may be implanted in a simpler manner while still leveraging the route of power and control signals (including stimulation and/or sensing) established via lead 1610 by use of the transfer element 1620.

In some examples, the electrode 1630 may comprise a freestanding electrode anchorable adjacent to or wrappable (e.g. cuff configuration) about the phrenic nerve 1535 and including wireless communication elements to communicate with the transfer element 1620 associated with lead 1610 and/or cuff electrode 1520.

FIG. 30F is a diagram schematically representing an example device 1650 comprising at least some of substantially the same features as device 1600 (FIG. 30E), except with a lead 1610 and cuff electrode 1520 being implanted and used to stimulate the phrenic nerve 1535, while a freestanding separate electrode 1630 is used to stimulate the hypoglossal nerve 1525 (or other upper airway-patency-related nerve). In some such examples, implantation may be simplified because just one lead (e.g. 1610) is tunneled subcutaneously from the site of implantation of the cuff electrode 1530 to the site of implantation (e.g. pectoral region) of the pulse generator 1510.

FIG. 30G is a diagram schematically representing at least a portion of an example device 1675 in which the freestanding separate electrode 1630 of device 1600 (FIG. 30E) and/or device 1650 (FIG. 30F) may comprise a microstimulator 1680 to stimulate a nerve 1685, such as (but not limited to) an upper airway patency-related nerve 1525, central sleep apnea-related nerve 1535, or other nerve. In some such examples, the microstimulator 1680 may comprise at least some of substantially the same features and attributes as described in Rondoni et al., WO 2017/087681, MICRO- STIMULATION SLEEP DISORDERED BREATHING (SDB) THERAPY DEVICE, published May 26, 2017, and which is hereby incorporated by reference in its entirety.

It will be understood that the microstimulator 1680 may be implemented as either one or both of the electrodes 1580, 1590 in FIG. 30D. In some such examples, a separate controller may coordinate operation of the respective microstimulators or one of the microstimulators may comprise a control portion (e.g. 3000 in FIG. 38A) which acts as a master to coordinate its own operation and the operation of the other microstimulator. Accordingly, it will be understood that in such examples, the microstimulators may be in wireless communication of power and controls signals (e.g. stimulation, sensing, etc.).

FIG. 30H is a diagram schematically representing an example device and/or example method to place a stimulation electrode transvenously in a patient's vasculature to stimulate an upper airway patency-related nerve 1525 (e.g. hypoglossal nerve) and a central sleep apnea-related nerve 1535 (e.g. phrenic nerve). In some examples, the device 1700 in FIG. 30H comprises at least some of substantially the same features and attributes as at least device 1550 in FIG. 30B, except for comprising transvenous electrodes 1720, 1730 instead of the cuff electrodes 1520, 1530 in FIG. 30B.

As shown in FIG. 30H, device 1700 comprises a bifurcated lead as in the device 1550 of FIG. 30B, which support a pair of respective transvenous electrodes 1720, 1730. Via single proximal lead portion 1560 and the respective distal lead portions 1562A, 1562B, the respective transvenous electrodes 1720, 1730 may be advanced within and through a patient's vasculature until the respective electrodes 1720, 1730 are positioned within a vein (e.g. 1722, 1732) adjacent the respective target nerves 1525, 1535. In some examples, the vein 1722 is a vein adjacent an upper airway patency-related nerve. In some such examples, the vein 1722 may be a ranine vein, lingual vein, or the like adjacent a hypoglossal nerve or other upper airway patency-related nerve. In some such examples, the vein 1732 may be pericardiophrenic vein (e.g. left pericardiophrenic vein), brachiocephalic vein (e.g. right brachiocephalic vein) and the like adjacent the phrenic nerve. In some examples, at least the single proximal lead portion 1560 facilitates and simplifies placement of the electrodes 1720, 1730 into their respective veins 1722, 1732.

FIG. 30I is a diagram schematically representing an example device 1750 and/or example method. In some examples, the device 1750 in FIG. 30I comprises at least some of substantially the same features and attributes as at least device 1700 in FIG. 30H, except for comprising just a single lead 1515B to place electrode 1730 transvenously within vein 1732 and comprising a freestanding separate electrode 1590 (instead of the transvenous electrode 1720 in FIG. 30H) adjacent an upper airway patency-related nerve 1525 (e.g. hypoglossal nerve).

In some examples, the freestanding separate electrode 1590 may comprise at least some of substantially the same features and attributes as the freestanding separate electrode (1590 in FIG. 30D and/or 1630 in FIG. 30F). Moreover, in some such examples, lead 1515B also may be implemented in a manner like lead 1610 which comprises a transfer element (e.g. 1620) to communicate with and support electrode 1590 as described in association with at least FIGS. 30E-30F.

As shown in FIG. 30J, in some examples the electrode 1590 in FIG. 30I may be implemented as a microstimulator 1746 of device 1745 in a manner similar to that described for microstimulator 1680 in FIG. 30G.

With regard to FIGS. 30I and 30J, it will be understood that in some examples the arrangement may be reversed such that a freestanding separate electrode (FIG. 30) or a microstimulator implementation of a freestanding separate electrode (FIG. 30J) may be implanted to stimulate the phrenic nerve 1535 and a lead and transvenous electrode may be delivered within a vasculature to stimulate an upper airway patency-related nerve to treat at least obstructive sleep apnea.

With regard to at least the example devices and/or method described in association with at least FIGS. 30A-31, it will be understood that in at least some examples such devices and/or methods may further comprise a sensor such as at least one of the sensors described in association with at least FIGS. 32-37 or combinations of such sensors. However, in some examples, a treatment device may comprise just a single sensor to detect central sleep apnea and in some examples, just a single sensor to detect obstructive sleep apnea. In some such examples, the single sensor to detect obstructive sleep apnea may comprise an accelerometer.

In some examples, a treatment device may comprise just a single sensor to detect central sleep apnea and to detect obstructive sleep apnea. In some such examples, the single sensor to detect both central sleep apnea and obstructive sleep apnea may comprise an accelerometer.

FIG. 30K is a diagram schematically representing an example device 1750 to stimulate an upper airway patency-related nerve 1525 and/or a central sleep apnea-related nerve 1535. In some examples, device 1750 comprises at least some of substantially the same features and attributes as device 1550 in FIG. 30B, except that respective electrodes 1752, 1754 are arranged in series instead of being arranged in parallel (e.g. FIGS. 30A, 30B), and with the device 1750 comprising a single lead 1755 rather than bifurcated lead portions 1562A, 1562B (e.g. FIG. 30B). Via the single lead 1755, proximal electrode 1752 can be placed adjacent first nerve 1525 and distal electrode 1754 can be placed adjacent second nerve 1535. In some instance, providing a single lead 1755 may facilitate tunneling between an electrode placement site and a site at which the pulse generator 1510 is implanted and/or may facilitate or simplify maneuvering the respective electrodes 1752, 1754 into position relative to the respective first nerve 1525 and second nerve 1535 to enable neurostimulation of those respective nerves. In some examples, one of the first nerve 1525 and second nerve 1535 may comprise an upper airway patency-related nerve and a respective other one of the first and second nerves 1525, 1535 may comprise a central sleep apnea-related nerve.

FIG. 31 is a diagram schematically representing an example device 1760 to stimulate an upper airway patency-related nerve 1525 and/or a central sleep apnea-related nerve 1535. In some examples, device 1760 comprises at least some of substantially the same features and attributes as device 1750 in FIG. 31, except that respective electrodes 1752 and/or 1754 may be positioned within vasculature portions 1762, 1764 of the patient's body. In some examples, vasculature portion 1762 comprises a different blood vessel (e.g. vein) than vasculature portion 1764.

Figure 32:
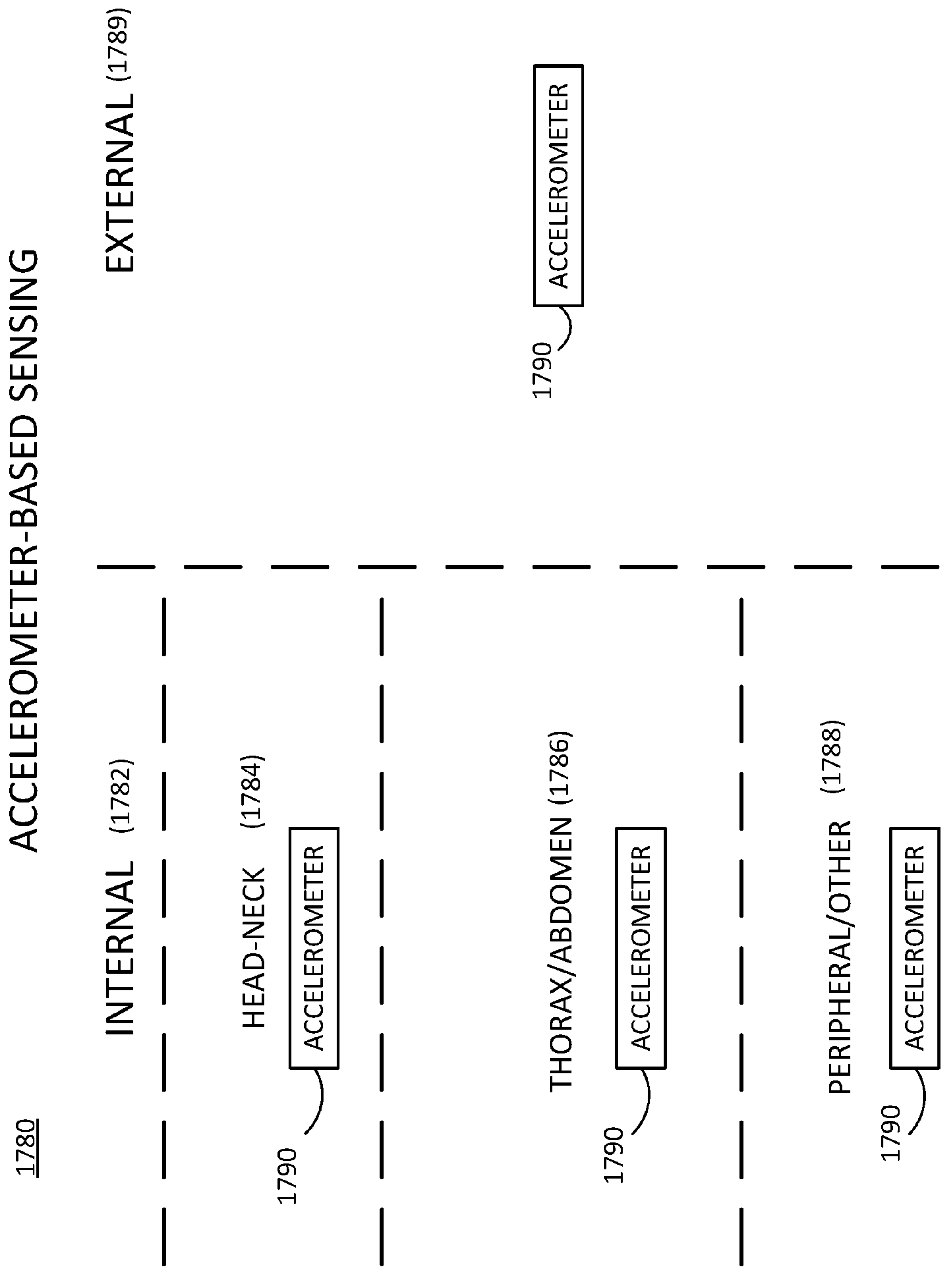
FIG. 32 is a diagram schematically representing example accelerometer-based sensing arrangements.

FIG. 32 is a diagram 1780 schematically representing accelerometer-based sensing, according to one example of the present disclosure. In some examples, the accelerometer-based sensing is associated with providing sleep disordered breathing (SDB) care which may comprise treating multi-type apnea as described in various examples throughout the present disclosure.

As shown in FIG. 32, in some examples at least one sensor includes an accelerometer-based sensor 1790 located internally (1782) within a patient while in some examples at least one sensor includes an accelerometer-based sensor (1790) located external (1789) to the patient. Such external sensors may be worn on the patient's body or spaced apart from the patient's body. In some examples, the at least one sensor including the accelerometer-based sensor may be located in a head-neck region 1784, a thorax/abdomen region 1786, and/or a peripheral/other region 1788 of a patient's body.

In some examples, regardless of location the respective accelerometer-based sensor(s) 1790 is provided without any associated stimulation elements within or external to the patient's body. In such examples, the information sensed via the accelerometer-based sensor(s) 1790 may be used for evaluating and/or diagnosing a patient.

However, in some examples, regardless of location the accelerometer-based sensor(s) 1790 is provided in association with at least one stimulation element to treat sleep disordered breathing behavior and/or other physiologic conditions.

At least some more specific example implementations of the sensor(s) shown in FIG. 32 are described and illustrated in association with at least FIGS. 33-37.

In some examples, the accelerometer 1790 may be used to sense heart rate variability (HRV), which in some examples may comprise sensing respiratory sinus arrrythmia (RSA) to implement the various examples previously described involving sensing of such physiologic information.

In some examples, the accelerometer 1790 and/or its implementation in treating sleep disordered breathing (e.g. obstructive sleep apnea, central sleep apnea, etc.) and related sensing may comprise at least some of substantially the same features and attributes as described and illustrated in Dieken et al. WO/2017/184753, ACCELEROMETER-BASED SENSING FOR SLEEP DISORDERED BREATHING (SDB) CARE, published Oct. 26, 2017.

Figure 33:
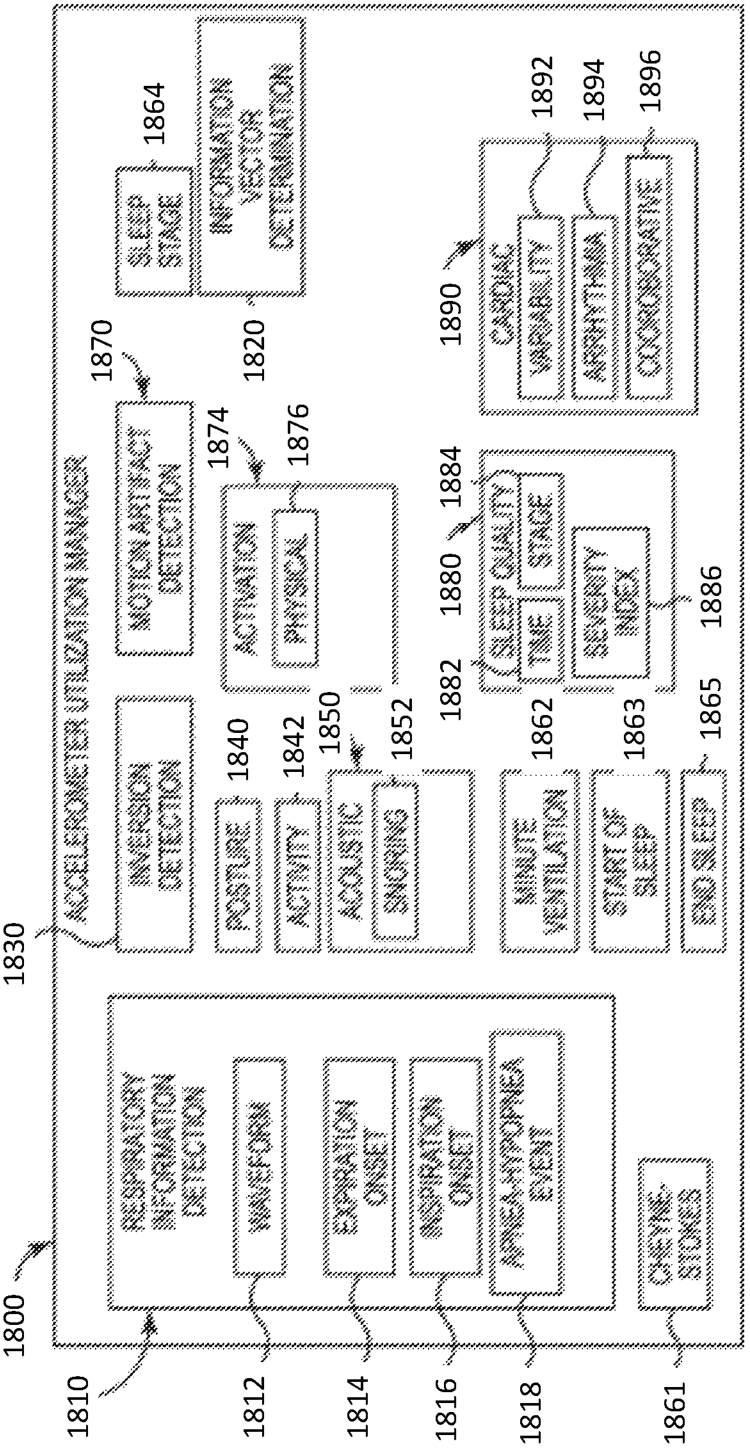
FIG. 33 is a diagram schematically representing an example accelerometer utilization engine.

FIG. 33 is a diagram schematically representing an accelerometer utlitization engine 1800, according to one example of the present disclosure. As shown in FIG. 33, in some examples the accelerometer utlitization engine 1800 comprises a respiratory information detection engine 1810, which includes a waveform function 1812, an expiration onset parameter 1814, an inspiration onset function 1816, and an apnea-hypopnea event detection engine 1818. In some examples, the apnea-hypopnea event detection engine 1818 is implemented via an apnea-hypopnea event detection engine 2300 as described later in association with at least FIG. 37. In some examples, the respiration information detection engine 1810 may comprise a respiration monitor and/or may sometimes be referred to as a respiration monitor.

In some examples, in general terms via waveform function 1812 the respiratory information detection engine 1810 detects and tracks a respiratory waveform, including but not limited to, detecting and tracking a respiratory rate, such as the time between onsets of inspiration or as the time between onsets of expiration. Accordingly, via waveform function 1812, the respiratory information detection engine 1810 can obtain a wide range of information, features, and characteristics discernible from a respiratory waveform sensed via one of the example accelerometer sensor arrangements and/or other types of sensors (FIG. 13).

Within this wide range of information, at least two characteristics of a respiratory waveform can play a prominent role in diagnosis, evaluation, and treatment of sleep disordered breathing. Accordingly, the respiratory information detection engine 1810 includes an expiration onset function 1814 and an inspiration onset function 1816.

Accordingly, in some examples the expiration onset function 1814 of respiration information detection engine 1810 in FIG. 33 can detect onset of expiration according to at least one of: (A) a second derivative of an amplitude of a respiration signal below a threshold (e.g. the sharpest peak); (B) a time after an onset of inspiration; and (C) a moving baseline for which time is calculated using the time of previous cycles and a respiratory rate. For instance, in some examples a respiration signal corresponds to a single axis (e.g. Z axis) of the accelerometer sensor, from whose output an amplitude can be determined and from which further processing may be applied, such as determining first and second derivatives.

Via this arrangement, the onset of expiration can be determined, and then used to trigger or terminate stimulation therapy as well as be used as a fiducial for general timing of respiratory evaluation and/or other therapeutic functions.

In some examples, prior to applying the above scheme, the signal may be processed with a lowpass and/or highpass filter to reject higher frequency motion artifact and lower frequency signals due to orientation with respect to the earth's gravity.

In some examples, the inspiration onset function 1816 of respiration information detection engine 1810 in FIG. 33 can detect onset of inspiration according to at least one of: (A) identification, after expiration onset, of a derivative of amplitude of respiration above a threshold; (B) time after onset of expiration: and (C) a moving baseline for which time is calculated using the time of previous cycles and a respiratory rate. Via this arrangement, the onset of inspiration can be determined, and then used to trigger or terminate stimulation therapy as well as be used as a fiducial for general timing of respiratory evaluation and/or other therapeutic functions. In some examples, prior to applying the above scheme, the signal may be processed with a lowpass and/or highpass filter to reject higher frequency motion artifact and lower frequency signals due to orientation with respect to the earth's gravity.

It will be understood that in some examples, both inspiration onset and expiration onset are used in combination as part of a more general scheme to trigger or terminate stimulation therapy as well as be used as a fiducial for general timing of respiratory evaluation and/or other therapeutic functions.

In some examples, a respiration monitor associated with at least one sensor is used to determine, at least one of an inspiratory phase and an expiratory phase, based on respiration information including at least one of respiratory period information and respiratory phase information. In some examples, a pulse generator is used to selectively stimulate an upper airway patency-related nerve via a stimulation element, during a portion of the inspiratory phase, based on respiration information from the respiration monitor. In some such examples, the pulse generator is optionally implantable.

In some examples, as shown in FIG. 33 the accelerometer utlitization engine 1800 comprises an inversion detection engine 1830. In some instances, a sensed respiratory signal may be inverted due to posture changes, which may occur depending on the axis orientation of the accelerometer sensor relative to a surface the patient is resting on. In some examples, such posture information is obtained in association with the later described posture function 1840 (FIG. 33).

Such inverted signals exhibit inspiration as having a predominantly negative slope and exhibit expiration as having a predominantly positive slope. In some examples, additional criteria (for declaring an inverted signal) include a duration of the positive slope portion of the waveform being longer than a duration of the negative slope portion of the waveform, as might be observable over several respiratory cycles. In some examples, additional criteria (for declaring an inverted signal) include a value of the mean of the signal being greater than a midpoint value, in which the midpoint is defined as one-half of a peak-to-peak amplitude. In the some examples, additional criteria (for declaring an inverted signal) include a maximum of absolute value of a second derivative at a location where the respiration signal is less than a respiration midpoint value.

By detecting an inverted respiratory waveform, the system may ensure that accurate tracking of patient respiration occurs, which in turn, may ensure that tracking and/or determinations made by the various engines, functions, parameters (e.g. FIG. 33-37) based on sensed respiratory information are reliable.

In some examples, accelerometer utilization engine 1800 comprises a posture function 1840. In at least this context, the term posture refers at least to identifying whether a patient is in a generally vertical position or a lying down position, such as a supine position, a prone position, a left side position (e.g. left lateral decubitus), a right side position (e.g. right lateral decubitus. In some instances, the term posture may sometimes be referred to as “body position.” Among other uses, sensed posture information may be indicative of behaviors from which sleep quality information or sleep disordered breathing (SDB) information may be determined.

In some examples, the posture function 1840 rejects non-posture components from an accelerometer sensor signal via low pass filtering relative to each axis of the multiple axes of the accelerometer sensor. In some examples, posture is at least partially determined via detecting a gravity vector from the filtered axes.

In some examples, accelerometer utilization engine 1800 comprises an activity function 1842, which can determine whether the patient is engaged in physical activity such as walking, running, swimming, etc. and determine related information such as total caloric expenditure. In some examples, such tracked information may provide a measure of overall health, overall health correlated with sleep disordered breathing therapy effectiveness, and/or other diagnostic information. In some examples, a sampling rate is increased when activity levels are changing quickly (e.g. measured values of sequential samples changes) and is decreased when the measured value of sequential samples are relatively stable. In some examples, the activity function 1842 operates in cooperation with other functions, such as posture function 1840 (FIG. 33).

In some examples, one potential classification protocol includes determining whether the patient is active or at rest via the posture function 1840 and/or activity function 1842 in FIG. 33. In some examples, when a vector magnitude of the acceleration measured via the accelerometer-based sensor meets or exceeds a threshold (optionally for a period of time), the measurement may indicate the presence of non-gravitational components indicative of non-sleep activity. In some examples, the threshold is about 1.15G. Conversely, measurements of acceleration of about 1G (corresponding to the presence of the gravitational component only) may be indicative of rest. In some examples, the posture function 1840 may reduce sampling to about 4 Hz to reduce processing power consumption.

In some examples, one potential classification protocol implemented via the posture function 840 includes determining whether at least an upper body portion (e.g. torso, head/neck) of the patient is in a generally vertical position (e.g. upright position) or lying down. In some examples, a generally vertical position may comprise standing or sitting. In some examples, this determination may observe the angle of the accelerometer-based sensor between the y-axis and the gravitational vector, which sometimes may referred to as a y-directional cosine. In the example, when such an angle is less than 40°, the measurement suggests the patient is in a generally vertical position, and therefore likely not asleep.

In some examples, processing this posture information may include excluding an inverted position, such as via inversion detection engine 1830 in FIG. 33.

In some examples, if the measured angle (e.g. a y-directional cosine) is greater than 40 degrees, then the measured angle indicates that the patient is lying down. In this case, one example protocol associated with the posture function 1840 includes classifying sub-postures, such as whether the patient is in a supine position, a prone position, or in a lateral decubitus position. In some examples, the protocol seeks to determine as soon as possible if the patient is in a supine position, which may be more likely to produce sleep disordered breathing.

Accordingly, after confirming a likely position of lying down, the protocol determines if the patient is in a supine position or a prone position. In some examples, the determination of a supine state is made when an absolute value of the z-directional cosine (the angle of the an accelerometer-based sensor between the z-axis (calibrated to represent the anterior-posterior axis of the patient’s body) and the gravitational vector is less than or equal to 45 degrees and the determination of a prone state is made when the absolute value of the z-directional cosine is greater than or equal to 135 degrees.

If neither of those criteria are satisfied, then the patient may be lying on their left or right side (e.g. a lateral decubitus position). Accordingly, the protocol performs a further classification via the pitch angle such that the patient is lying on their right side if the pitch angle is less than or equal to negative 45 degrees or greater than or equal to negative 135 degrees. However, the protocol determines that the patient is lying on their left side if the pitch angle is greater than or equal to 45 degrees or the pitch angle is less than or equal to 135 degrees. In some examples, a similar determination may be made using directional cosines.

In some examples, accelerometer utlitization engine 1800 comprises an acoustic engine 1850 to determine if snoring is occurring per snoring function 852. One arrangement in which acoustic engine 1850 may determine snoring corresponds to placement of the accelerometer sensor at the distal end of a stimulation lead, which is secured to an upper airway-patency related nerve. Via this arrangement, the accelerometer sensor will be located in close physical proximity to the physical manifestations and effects of snoring at the upper airway. In some examples, a similar snoring-pertinent placement of the accelerometer sensor can be made when the accelerometer sensor is physically independent of a lead or the pulse generator (e.g. 1435 in FIG. 29).

In some examples, acoustic engine 1850 can use other acoustically-sensed information such as an acoustic sensor 2244 as described later in association with at least FIG. 35. This other acoustic information may be used in addition to, or instead of, the acoustic information obtained via one of the example accelerometer sensor implementations.

In some examples, the accelerometer utlitization engine 1800 comprises a minute ventilation engine 1862 to determine and/or track minute ventilation, which can provide a correlation of motion with tidal volume and act as a significant corollary to apnea detection.

In some examples, the accelerometer utlitization engine 1800 comprises a Cheyne-Stokes respiration engine 1861 to determine and/or track Cheyne-Stokes respiration, which can provide a correlation of motion with changes in tidal volume and act as a significant corollary to apnea detection.

In some examples, accelerometer utlitization engine 1800 comprises a start-of-sleep detection engine 1863. In some instances, start-of-sleep may sometimes be referred to as sleep onset. Via utilization engine 863, once a treatment period has been initiated, delivery of stimulation is delayed until start-of-sleep has been detected. Doing so can facilitate the patient falling asleep before the first therapeutic stimulation occurs while also preventing therapeutic stimulation from beginning too late. In some examples, detecting start-of-sleep via utilization engine 1863 is implemented via tracking posture (e.g. 1840), activity (e.g. 1842), cardiac information (e.g. 1890, 1892), and/or trends of respiratory rates (e.g. 1810). In some examples, accelerometer utilization engine 1863 is subject to a manual therapy activation function controllable by a patient such that therapy may not be initiated even when start-of-sleep is detected if the patient has implemented an off or "no therapy" mode. In some examples, this manual therapy activation function can ensure that stimulation therapy does not become initiated during non-sleep hours when the patient is relatively sedentary (e.g. prolonged sitting, driving, etc.) or in a horizontal position, such as laying in a dentist chair, laying on the beach, and the like.

In some examples, accelerometer utilization engine 1800 comprises a motion artifact detection engine 1870. In one aspect, motion signals have a significantly greater amplitude than respiration signals, and therefore the motion signals are extracted from a respiratory waveform or otherwise rejected. In some examples, this extraction may be implemented via an awareness of motion associated with an X axis or Y axis of an accelerometer sensor having signal power significantly greater than the signal power of a Z axis in the accelerometer sensor, such as where the accelerometer sensor is implanted in some examples such that its Z axis is generally parallel to an anterior-posterior axis of the patient's body. If a patient's respiration signal is largest in a particular axis (not necessarily aligned with one of X, Y, Z), motion artifact can be rejected by filtering signals not aligned with the axis where respiration is largest. In one aspect, motion signals sensed via the accelerometer sensor can be distinguished from the respiration signals sensed via the accelerometer sensor according to the high frequency content above a configurable threshold.

In some examples, accelerometer utlitization engine 1800 comprises an activation engine 1874. In some examples, the activation engine 1874 provides at least partial control over therapy, such as when a remote control (physician or patient) is not available. Such partial control includes at least pausing therapy, starting therapy, stopping therapy, and the like. In some examples, the activation engine 1874 operates according to physical control mode 1876, such as tapping the chest (or pertinent body portion at which the accelerometer sensor is located) a certain number of times within a configurable time period (e.g. three strong taps within two seconds). In some examples, this physical control mode 1876 may act as an alternate therapy deactivation mechanism, such as when the stimulation system is accidentally activated, such as upon an incorrect determination of sleep via an automatic therapy initiation mechanism.

In some examples, accelerometer utlitization engine 1800 comprises a sleep stage determination engine 1864 by which sleep stages can be determined. In some examples, such determination is made according to the relative stability of respiratory rate throughout the treatment period (during sleeping hours). In some examples, engine 1864 determines and tracks the number of minutes awake, minutes in bed, posture, sleep/wake cycle, and/or number and depth of REM periods. In some examples, accelerometer utlitization engine 1800 comprises a sleep quality engine 1880 to determine sleep quality according to a combination of a sleep time parameter 1882, a sleep stage parameter 1884, and a severity index parameter 1886 (e.g. AHI measurement). In some instances, the determined sleep quality is communicated to at least the patient to affirm the patient when sleep quality is good and to encourage and challenge the patient when sleep quality is poor. The communication may suggest lifestyle changes and/or increased therapy compliance.

In some examples, a sleep function (e.g. 1864 in FIG. 33) may determine, at least partially via at least one sensing element, sleep stages in which a determination of at least some of the determined sleep stages may be implemented via at least one of activity information, posture information, respiratory rate information, respiratory rate variability (RRV) information, heart rate variability (HRV) information, and heart rate information.

In some examples, accelerometer utlitization engine 1800 comprises a cardiac detection engine 1890 including a variability parameter 1892, an arrhythmia parameter 1894, and a corroborative parameter 1896. In some examples, an accelerometer of one of the example devices may enable acoustic detection of cardiac information, such as heart rate. In some examples, measuring the heart rate includes sensing heart rate variability (1934 in FIG. 34B) per parameter 1892 (FIG. 33).

In some examples, accelerometer 1790 enables detection of cardiac information via a seismocardiogram (1922 in FIG. 34A) or a ballistocardiogram (e.g. 1924 in FIG. 34A) waveforms, including QRS complexes. In some examples, this cardiac information may provide heart rate variability information per heart rate variability sensing function 1930 (FIG. 34B) and parameter 1892 (FIG. 33).

In some examples, via one of the accelerometer sensors, one can sense respiratory information, such as but not limited to, a respiratory rate. In some examples, whether sensed via an accelerometer sensor alone or in conjunction with other sensors, one can track cardiac information and respiratory information simultaneously by exploiting the behavior of manner in which the cardiac waveform may vary with respiration.

In some examples, the variability parameter 1892 (FIG. 33) tracks heart-rate variability. In some examples, the heart-rate variability may correlate with autonomic function. In one aspect, tracking such heart-rate variability (HRV) is based on a strong beat-detection method providing reasonably accurate R-R intervals and associated cardiac trends. It will be understood that R represents a peak of a QRS complex of a cardiac waveform (e.g. an ECG wave, seismocardiogram, or ballistocardiogram), and the R-R interval corresponds to an interval between successive "R"s in the cardiac waveform.

Figure 34A:
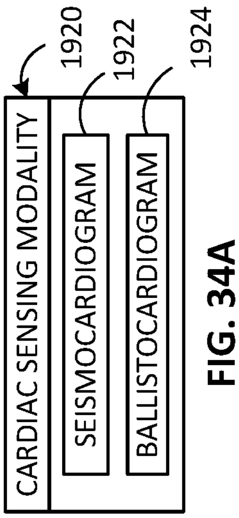
FIG. 34A is a block diagram schematically representing an example cardiac sensing modality function.
Figure 34B:
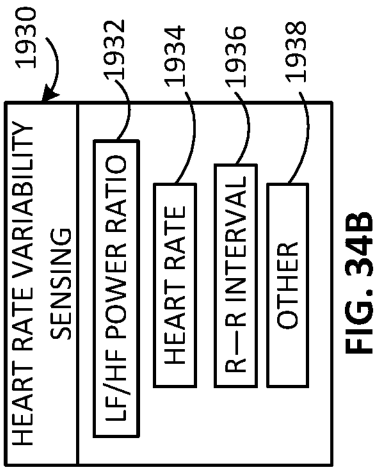
FIG. 34B is a block diagram schematically representing an example heart rate variability (HRV) function.

In some examples, the heart-rate variability may be tracked according to several different frequency bands, such as a very-low frequency (VLF) band, a low frequency (LF) band, and a high frequency (HF) band. In some examples, the very-low frequency (VLF) band may involve frequencies of about 0.005 Hz to about 0.04 Hz, which may correspond to vasomotion and thermoregulation. In some examples, the low frequency (LF) band may involve frequencies of about 0.04 Hz to about 0.15 Hz, which may correspond to sympathetic and parasympathetic activity. In some examples, the low frequency (LF) band may involve frequencies of about 0.15 Hz to about 0.50 Hz, which may correspond to parasympathetic activity and respiration. With this in mind, the heart-rate variability (HRV) parameter 1892 may comprise a heart-rate variability sensing function 1930 as shown in FIG. 34B, which comprises a LF/HF ratio parameter 1932, a heart rate parameter 1934, a R-R interval parameter 1936, and an other parameter 1938.

In some examples, per the LF/HF ration parameter 1932, the heart-rate variability sensing function 1930 tracks a ratio of low frequency power to high frequency power (a LF/HF ratio) over time, which provides an estimate of sympatho-vagal balance. A significant decrease in the LF/HF ratio indicates an increase in parasympathetic dominance, which may indicate sleep onset in some examples. For instance, in some examples a decrease of about 25 percent in the LF/HF ratio may be indicative of sleep onset. In some examples, a decrease of about 50 percent in the LF/HF ratio may indicate sleep onset.

In some examples, the heart-rate variability via parameter 1892 (FIG. 33) may provide for secondary confirmation for other features, such as the overall cardiovascular health of the patient.

In some examples, the heart-rate variability per parameter 1892 may be used to determine sleep latency, e.g. a length of time to transition from full wakefulness to sleep, such as non-rapid-eye-movement (NREM) sleep. In addition, this heart-rate variability information may be employed to identify sleep onset, i.e. the transition from wakefulness to sleep. For instance, a decrease in heart rate is associated with sleep onset. In some examples, this information may enable operation of a stimulation onset determination.

In some examples, the heart-rate variability per parameter 1892 can be employed to distinguish and/or determine sleep stages (including REM), such as in association with sleep stage function 1864 (FIG. 33). In some instances, determining sleep stage(s) via HRV parameter 1892 may be more accurate than activity-based determinations of sleep stages.

Figure 37:
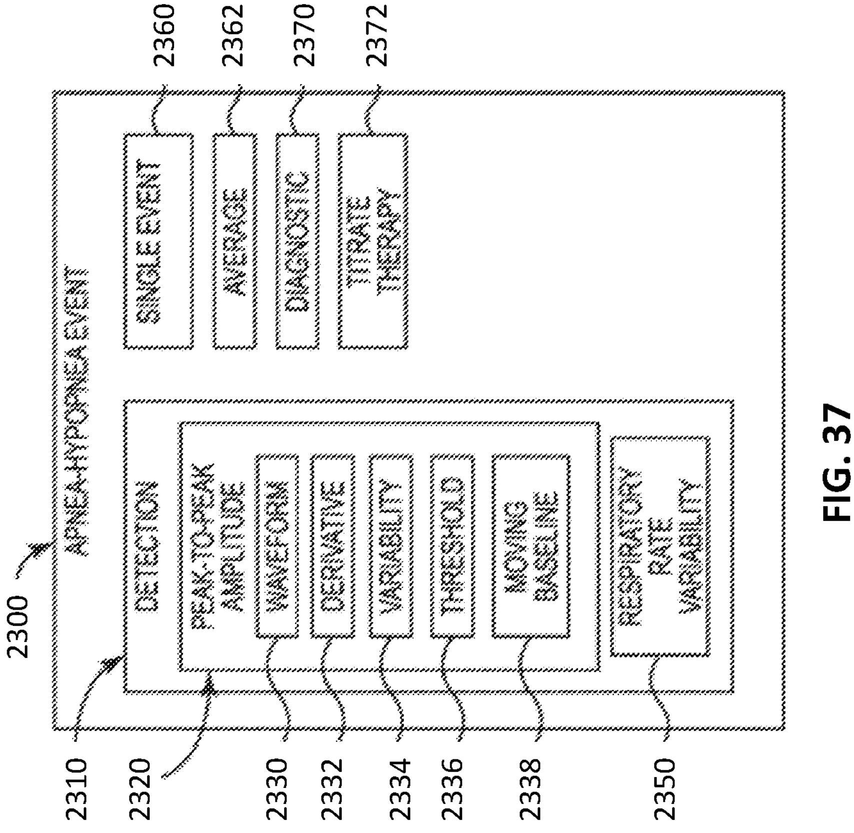
FIG. 37 is a block diagram schematically representing an example apnea-hypopnea event management engine.

In some examples, per heart rate parameter 1934 in FIG. 34B, a decrease in heart rate may correspond to sleep onset, which also may be accompanied by an increase in the R-R interval (RRI), which is tracked and/or determined via parameter 1936. In some examples, an increase in the R-R interval (RRI) and/or a decrease in variability of a respiratory rate interval (RRI) may be indicative of sleep onset. In some examples, a respiratory rate interval (RRI) is tracked and/or determined via at least respiratory information detection engine 1810 (FIG. 33) and/or respiratory rate variability function 2350 (FIG. 37).

In some examples, the cardiac variability information per parameter 1892 (FIG. 33) may be employed in association with respiratory rate information and/or other information to determine sleep onset.

In some examples, arrhythmias are detected and tracked via parameter 1894 (FIG. 33) with such arrhythmias including, but not limited to, atrial fibrillation.

In some examples, via corroborative parameter 1896 (FIG. 33), the cardiac detection engine 1890 can provide a corroboration or secondary confirmation of other features detected and tracked via an accelerometer-based sensor.

In some examples, the accelerometer utilization engine 1800 comprises an information vector determination engine 1820 to determine an information vector from which neurostimulation therapy parameters can be determined and/or adjusted such as via a stimulation manager. In some examples, the information vector is determined according to sensed patient information, which can comprise any combination of the various types of respiratory and non-respiratory information identified via accelerometer utilization management engine 1800, and as represented via at least elements 1810-1890 in FIG. 33. In some examples, this sensed patient information (from which the information vector is determined) also comprises sensed information from any one of, or combination of, the sensors in sensor type array 2200 in FIG. 35. In some examples, the sensed patient information (from which the information vector is determined) also comprises apnea-hypopnea information as sensed or determined via apnea-hypopnea detection engine 1300 in FIG. 15.

Figure 34C:
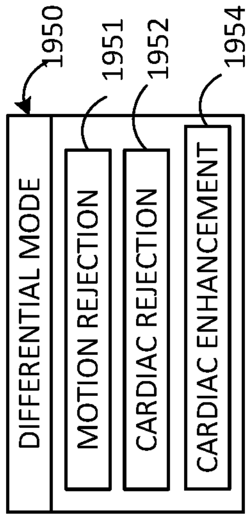
FIG. 34C is a block diagram schematically representing an example differential mode function.

FIG. 34C is a block diagram schematically representing a differential mode engine 1950, according to one example of the present disclosure. In some examples, the differential mode engine 1950 includes a motion artifact rejection parameter 1951, a cardiac rejection parameter 1952 and/or a cardiac enhancement parameter 1954. In some examples, upon at least two accelerometer sensors being implemented as part of a neurostimulation system (in accordance with the examples of the present disclosure), a differential mode of operation is implemented in which a comparison or combination of the signals from the two different accelerometer sensors takes place. In some examples, a difference between the two signals may be used to reject motion artifacts and/or cardiac artifacts, such as via respective parameters 1951, 1952. However, in some examples, a difference between the two signals may be used to enhance cardiac or respiratory signals via parameter 1954.

Figure 35:
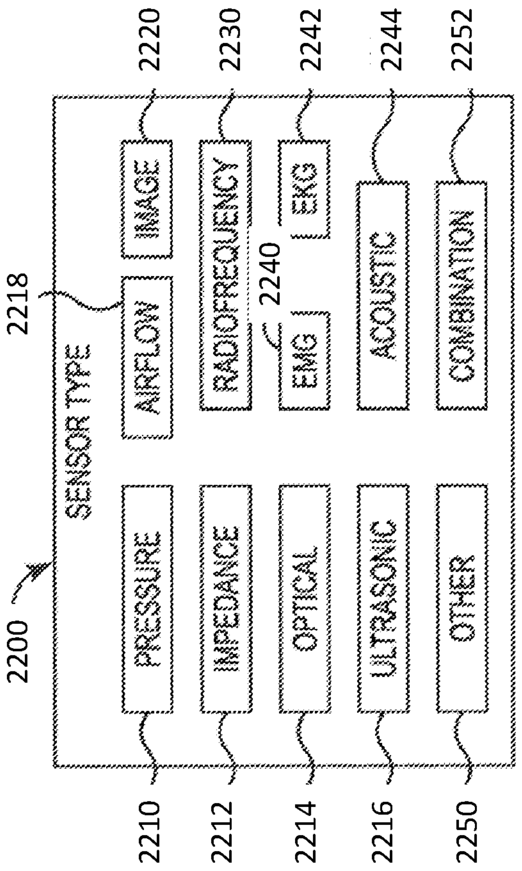
FIG. 35 is a block diagram schematically representing example sensor types.

FIG. 35 is a block diagram schematically representing a sensor type 1100, according to one example of the present disclosure. In some examples, an example device and/or method may employ sensing modalities other than, or in addition to, an accelerometer sensor and may employ sensing modalities other than, or in addition to, cardiac-related sensing as described herein whether or not such cardiac-related sensing is based on accelerometer sensing. It will be further understood that any cardiac-related sensing described herein may act as a sole sensing modality for an implanted device, as a primary sensing modality with other/additional secondary sensing modalities (e.g. respiration, non-respiratory, etc.), or as a second sensing modality to another primary sensing modality (or modalities) whether or not the primary sensing modality is respiration-related.

As shown in FIG. 35, sensor type array 1200 comprises various types of sensor modalities 2210-2252, any one of which may be used for determining, obtaining, and/or monitoring respiratory information, cardiac information, sleep quality information, sleep disordered breathing-related information, and/or other information related to providing or evaluating patient therapy or general patient well-being.

As shown in FIG. 35, in some examples sensor type 2200 comprises the modalities of pressure 2210, impedance 2212, airflow 2218, radiofrequency (RF) 2230, optical 2214, electromyography (EMG) 2240, electrocardiography (EKG) 2242, ultrasonic 2216, acoustic 2244, and/or other 2250. In some examples, sensor type 2200 comprises a combination 2252 of at least some of the various sensor modalities 2200-2250.

Any one of these sensor modalities, or combinations thereof, may be used in association with, or even independently from, one of the accelerometer sensors previously described in examples of the present disclosure. In some examples, one of the these sensor modalities, or combinations thereof, may be used to corroborate, supplement, and/or evaluate information sensed via one of the accelerometer sensors previously described in examples of the present disclosure.

In some examples, to the extent that at least some of the accelerometer sensors (FIGS. 32-37) may eliminate or minimize tunneling to place an accelerometer sensor, at least some of the additional sensor modalities in FIG. 35 also may be external sensors or involve minimally invasive sensing implementations, which minimize tunneling or other significant intrusions.

It will be understood that, depending upon the attribute being sensed, in some instances a given sensor modality identified within FIG. 35 may include multiple sensing components while in some instances, a given sensor modality may include a single sensing component. Moreover, in some instances, a given sensor modality identified within FIG. 35 and/or accelerometer sensor (FIGS. 32-37) may include power circuitry, monitoring circuitry, and/or communication circuitry. However, in some instances a given sensor modality in FIG. 35 or accelerometer sensor (FIGS. 32-37) may omit some power, monitoring, and/or communication circuitry but may cooperate with such power, monitoring or communication circuitry located elsewhere.

In some examples, a pressure sensor 2210 may sense pressure associated with respiration and can be implemented as an external sensor and/or as an implantable sensor. In some instances, such pressures may include an extrapleural pressure, intrapleural pressures, etc. For example, one pressure sensor 2210 may comprise an implantable respiratory sensor, such as that disclosed in Ni et al. U.S. Patent Publication 2011-0152706, published on Jun. 23, 2011, titled METHOD AND APPARATUS FOR SENSING RESPIRATORY PRESSURE IN AN IMPLANTABLE STIMULATION SYSTEM.

In some instances, pressure sensor 2210 may include a respiratory pressure belt worn about the patient's body.

In some examples, pressure sensor 2210 comprises piezoelectric element(s) and may be used to detect sleep disordered breathing (SDB) events (e.g. apnea-hypopnea events), to detect onset of inspiration, and/or detection of an inspiratory rate, etc.

As shown in FIG. 35, in some examples one sensor modality includes air flow sensor 2218, which can be used to sense respiratory information, sleep disordered breathing-related information, sleep quality information, etc. In some instances, air flow sensor 2218 detects a rate or volume of upper respiratory air flow.

As shown in FIG. 35, in some examples one sensor modality includes impedance sensor 2212. In some examples, impedance sensor 2212 may be implemented in some examples via various sensors distributed about the upper body for measuring a bio-impedance signal, whether the sensors are internal and/or external. In some examples, the impedance sensor 2212 senses an impedance indicative of an upper airway collapse.

In some instances, the sensors are positioned about a chest region to measure a trans-thoracic bio-impedance to produce at least a respiratory waveform.

In some instances, at least one sensor involved in measuring bio-impedance can form part of a pulse generator, whether implantable or external. In some instances, at least one sensor involved in measuring bio-impedance can form part of a stimulation element and/or stimulation circuitry. In some instances, at least one sensor forms part of a lead extending between a pulse generator and a stimulation element.

In some examples, impedance sensor 2212 is implemented via a pair of elements on opposite sides of an upper airway.

In some examples, impedance sensor 2212 may take the form of electrical components not formally part of one of the previously described devices and/or methods. For instance, some patients may already have a cardiac therapy device (e.g. pacemaker, defibrillator, etc.) implanted within their bodies, and therefore have some cardiac leads implanted within their body. Accordingly, the cardiac leads may function together or in cooperation with other resistive/electrical elements to provide impedance sensing.

In some examples, whether internal and/or external, impedance sensor(s) 2212 may be used to sense an electrocardiogram (EKG) signal.

In some examples, impedance sensor 2212 is used to detect sleep disordered breathing (SDB) events (e.g. apnea-hypopnea events), to detect onset of inspiration, and/or detection of an inspiratory rate, etc.

In some examples, radiofrequency sensor 2230 shown in FIG. 35 enables non-contact sensing of various physiologic parameters and information, such as but not limited to respiratory information, cardiac information, motion/activity, and/or sleep quality. In some examples, radiofrequency sensor 2230 enables non-contact sensing of other physiologic information. In some examples, radio-frequency (RF) sensor 2230 determines chest motion based on Doppler principles. The sensor 2230 can be located anywhere within the vicinity of the patient, such as various locations within the room (e.g. bedroom) in which the patient is sleeping. In some examples, the sensor 2230 is coupled to a monitoring device to enable data transmission relative to other components of an example neurostimulation therapy system and storage in such other components.

In some examples, one sensor modality may comprise an optical sensor 2214 as shown in FIG. 35. In some instances, optical sensor 2214 may be an implantable sensor and/or external sensor. For instance, one implementation of an optical sensor 2214 comprises an external optical sensor for sensing heart rate and/or oxygen saturation via pulse oximetry. In some instances, the optical sensor 2214 enables measuring oxygen desaturation index (ODI). In some examples, the optical sensor 2214 comprises an external sensor removably couplable on the finger of the patient.

In some examples, optical sensor 2214 can be used to measure ambient light in the patient's sleep environment, thereby enabling an evaluation of the effectiveness of the patient's sleep hygiene and/or sleeping patterns.

As shown in FIG. 35, in some examples one sensor modality comprises EMG sensor 2240, which records and evaluates electrical activity produced by muscles, whether the muscles are activated electrically or neurologically. In some instances, the EMG sensor 2240 is used to sense respiratory information, such as but not limited to, respiratory rate, apnea events, hypopnea events, whether the apnea is obstructive or central in origin, etc. For instance, central apneas may show no respiratory EMG effort.

In some instances, the EMG sensor 2240 may comprise a surface EMG sensor while, in some instances, the EMG sensor 2240 may comprise an intramuscular sensor. In some instances, at least a portion of the EMG sensor 2240 is implantable within the patient's body and therefore remains available for performing electromyography on a long term basis.

In some examples, one sensor modality may comprise EKG sensor 2242 which produces an electrocardiogram (EKG) signal. In some instances, the EKG sensor 2242 comprises a plurality of electrodes distributable about a chest region of the patient and from which the EKG signal is obtainable. In some instances, a dedicated EKG sensor(s) 2242 is not employed, but other sensors such as an array of bio-impedance sensors 2212 are employed to obtain an EKG signal. In some instances, a dedicated EKG sensor(s) is not employed but EKG information is derived from a respiratory waveform, which may be obtained via any one or several of the sensor modalities in sensor type array 2200 of FIG. 35. In some examples, EKG sensor 2242 is embodied or at least implemented in part as at least one of the accelerometer sensors (FIGS. 32-37).

In some examples, an EKG signal obtained via EKG sensor 2242 may be combined with respiratory sensing (via pressure sensor 2210, impedance sensor 2212, and/or an accelerometer sensor) to determine minute ventilation, as well as a rate and phase of respiration. In some examples, the EKG sensor 2242 may be exploited to obtain respiratory information.

In some examples, EKG sensor 2242 is used to detect sleep disordered breathing (SDB) events (e.g. apnea-hypopnea events), to detect onset of inspiration, and/or detection of an inspiratory rate, etc.

As shown in FIG. 35, in some examples one sensor modality includes an ultrasonic sensor 2216. In some instances, ultrasonic sensor 2216 is locatable in close proximity to an opening (e.g. nose, mouth) of the patient's upper airway and via ultrasonic signal detection and processing, may sense exhaled air to enable determining respiratory information, sleep quality information, sleep disordered breathing information, etc. In some instances, ultrasonic sensor 2216 may comprise at least some of substantially the same features and attributes as described in association with at least Arlotto et al. PCT Published Patent Application 2015-014915 published on Feb. 5, 2015.

In some examples, acoustic sensor 2244 comprises piezoelectric element(s), which sense acoustic vibration. In some implementations, such acoustic vibratory sensing may be used to detect sleep disordered breathing (SDB) events (e.g. apnea-hypopnea events), to detect onset of inspiration, and/or detection of an inspiratory rate, etc. In some examples, acoustic sensor 2244 is implemented via one of the accelerometer sensors in the examples of the present disclosure as previously described in association with at least acoustic engine 1850 in FIG. 33. In some examples, a therapy system can comprise at least two acoustic sensors, such as a first acoustic sensor implemented via an accelerometer sensor (FIGS. 32-37) and a second acoustic sensor implemented via another type of acoustic sensing (e.g. piezoelectric).

In some examples, acoustic sensor 2244 detects snoring information, which may be used in detection, evaluation, and/or modification of sleep-related information and/or therapy parameters.

In some examples, one of the sensor types 2200 or a combination of such sensors senses local or gross motion, such as snoring, inspiration/expiration, etc., which may be indicative to sleep quality, sleep disordered breathing events, general respiratory information, etc.

In some examples, information sensed via one of the sensors in FIG. 35, such as but not limited to motion information, can be used in a training mode of an implantable neurostimulation system (as described herein) to correlate the patient's respiration with the sensed motion.

In some examples, several sensor modalities of the sensory type array 1200 are combined, as represented via combination identifier 2252.

Figure 36:
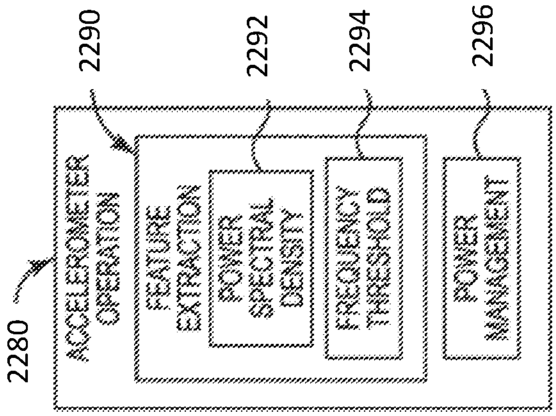
FIG. 36 is a block diagram schematically representing example accelerometer operation functions.

FIG. 36 is a block diagram schematically representing accelerometer operation engine 2280, according to one example of the present disclosure. As shown in FIG. 36, in some examples accelerometer operation engine 2280 comprises a feature extraction function 2290 and a power management function 2296. In general terms, the feature extraction function 2290 determines which features to extract from the different axis signals and/or meta-vectors (e.g. combined axis signals). In some examples, such feature extraction is implemented via a power spectral density parameter 2292 and a frequency threshold parameter 2294. For instance, a cardiac-related information obtained via an accelerometer sensor, such as via engine 1890 in FIG. 33, can have a different signature (e.g. recognizable waveform characteristics) than respiration-related information. In some examples, via parameter 2292 some such cardiac signals can be classified as having a dominant power spectral density meeting or exceeding a frequency threshold (as set via parameter 2294) while respiratory signals can be classified as having a dominant power spectral density which falls below the same frequency threshold. Stated differently, the power spectral density parameter 2292 facilitates identifying sensed cardiac information as a first portion of the sensed accelerometer signals which exhibit substantial power at relatively higher frequencies and identifying sensed respiratory information as a second portion of the sensed accelerometer signals which exhibit substantial power at relative lower frequencies.

Upon differentiating cardiac information and respiratory information from sensed accelerometer signals, the various devices, managers, engines, functions, parameters as described throughout examples of the present disclosure may be employed to determine other physiologic information, which may or may not relate to detecting, evaluating, diagnosing, and/or treating sleep disordered breathing behavior.

In some examples, the power management function 2296 provides for managing power used for sensing. In some instances, via function 2296 a higher sampling rate can be used at an accelerometer sensor when SDB events are detected while a lower sampling rage can be used during normal respiration. In some instances, power is not supplied (or greatly reduced) to an accelerometer sensor when stimulation is delivered via an open loop mode.

In some examples, the power management function 2296 is associated with at least one sensing element of a SDB care device to selectively activate and/or de-activate at least one function of the at least one sensing element at selective periods of time based on information sensed via the at least one sensor. In some examples, the sensed information comprises posture information. In some examples, the posture information comprises changes in posture and/or a lack of change in posture. In some examples, the sensed information comprises cardiac information or other information which is in addition to or instead of the posture information. In some examples, the at least one function of the at least one sensor comprises a posture detection or tracking function (e.g. position tracking). As just one of many examples, the power management function 2296 may deactivate posture detection after detecting a generally vertical posture and activate posture detection upon sensed respiratory information (e.g. respiratory variability) determining sleep. Of course, in some examples the at least one function which is selectively activated or de-activated may comprise a function other than posture or in addition to posture.

In some examples, the at least one sensing element governed via the power management function 2296 comprises an accelerometer-based sensor. In some examples, the at least one sensing element governed via the power management function 2296 includes other sensing modalities instead of an accelerometer-based sensor or in addition to an accelerometer-based sensor.

Figure 38A:
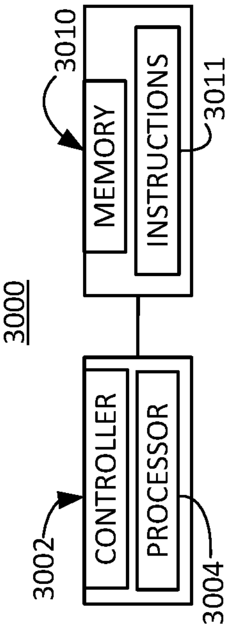
FIG. 38A is a block diagram schematically representing an example control portion.

FIG. 38A is a block diagram schematically representing an example control portion 3000. In some examples, control portion 3000 provides one example implementation of a control portion forming a part of, implementing, and/or generally managing stimulation elements, pulse generators, sensors, and related elements, devices, user interfaces, instructions, information, engines, elements, functions, actions, and/or methods, as described throughout examples of the present disclosure in association with FIGS. 1-37.

In some examples, control portion 3000 includes a controller 3002 and a memory 3010. In general terms, controller 3002 of control portion 3000 comprises at least one processor 3004 and associated memories. The controller 3002 is electrically couplable to, and in communication with, memory 3010 to generate control signals to direct operation of at least some of the stimulation elements, pulse generators, sensors, and related elements, devices, user interfaces, instructions, information, engines, elements, functions, actions, and/or methods, as described throughout examples of the present disclosure. In some examples, these generated control signals include, but are not limited to, employing instructions 3011 and/or information 3012 stored in memory 3010 to at least direct and manage treatment of sleep disordered breathing such as obstructive sleep apnea and/or central sleep apnea, sensing physiologic information including but not limited to respiratory information, heart rate, and/or monitoring sleep disordered breathing, etc. as described throughout the examples of the present disclosure in association with FIGS. 1-37. In some instances, the controller 3002 or control portion 3000 may sometimes be referred to as being programmed to perform the above-identified actions, functions, etc. In some examples, at least some of the stored instructions 3011 are implemented as, or may be referred to as, a treatment engine. In some examples, at least some of the stored instructions 3011 and/or information 3012 may form at least part of, and/or, may be referred to as a treatment engine.

In response to or based upon commands received via a user interface (e.g. user interface 3020 in FIG. 38C) and/or via machine readable instructions, controller 3002 generates control signals as described above in accordance with at least some of the examples of the present disclosure. In some examples, controller 3002 is embodied in a general purpose computing device while in some examples, controller 3002 is incorporated into or associated with at least some of the stimulation elements, pulse generators, sensors, and related elements, devices, user interfaces, instructions, information, engines, functions, actions, and/or method, etc. as described throughout examples of the present disclosure.

For purposes of this application, in reference to the controller 3002, the term "processor" shall mean a presently developed or future developed processor (or processing resources) that executes machine readable instructions contained in a memory. In some examples, execution of the machine readable instructions, such as those provided via memory 3010 of control portion 3000 cause the processor to perform the above-identified actions, such as operating controller 3002 to implement the apnea treatment as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium), as represented by memory 3010. In some examples, the machine readable instructions may comprise a sequence of instructions, a processor-executable machine learning model, or the like. In some examples, memory 3010 comprises a computer readable tangible medium providing non-volatile storage of the machine readable instructions executable by a process of controller 3002. In some examples, the computer readable tangible medium may sometimes be referred to as, and/or comprise at least a portion of, a computer program product. In other examples, hard wired circuitry may be used in place of or in combination with machine readable instructions to implement the functions described. For example, controller 3002 may be embodied as part of at least one application-specific integrated circuit (ASIC), at least one field-programmable gate array (FPGA), and/or the like. In at least some examples, the controller 3002 is not limited to any specific combination of hardware circuitry and machine readable instructions, nor limited to any particular source for the machine readable instructions executed by the controller 3002.

In some examples, control portion 3000 may be entirely implemented within or by a stand-alone device.

In some examples, the control portion 3000 may be partially implemented in one of the apnea treatment devices (or portions thereof) and partially implemented in a computing resource separate from, and independent of, the apnea treatment devices (or portions thereof) but in communication with the apnea treatment devices (or portions thereof). For instance, in some examples control portion 3000 may be implemented via a server accessible via the cloud and/or other network pathways. In some examples, the control portion 3000 may be distributed or apportioned among multiple devices or resources such as among a server, an apnea treatment device (or portion thereof), and/or a user interface.

Figure 38B:
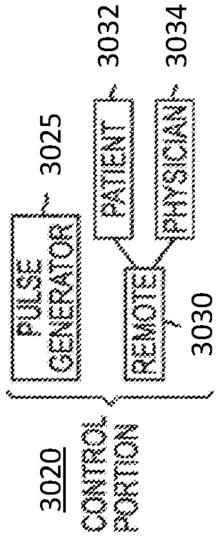
FIG. 38B is a diagram schematically representing at least some example different modalities of the control portion.
Figure 38C:
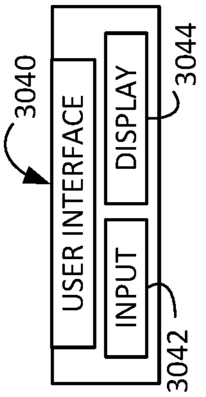
FIG. 38C is a block diagram schematically representing an example user interface.

In some examples, control portion 3000 includes, and/or is in communication with, a user interface 3020 as shown in FIG. 38C. In some examples, user interface 3020 comprises a user interface or other display that provides for the simultaneous display, activation, and/or operation of at least some of the stimulation elements, pulse generators, sensors, and related elements, devices, instructions, information, engines, functions, and/or method, etc., as described in association with FIGS. 1-37. In some examples, at least some portions or aspects of the user interface 3020 are provided via a graphical user interface (GUI), and may comprise a display 3024 and input 3022.

FIG. 38B is a diagram schematically illustrating at least some example implementations of a control portion by which the control portion 3000 (FIG. 38A) can be implemented, according to one example of the present disclosure. In some examples, control portion 3000 is entirely implemented within or by an IPG assembly 3025, which has at least some of substantially the same features and attributes as a pulse generator (e.g. 1435) as previously described throughout the present disclosure. In some examples, control portion 3000 is entirely implemented within or by a remote control 3030 (e.g. a programmer) external to the patient's body, such as a patient control 3032 and/or a physician control 3034. In some examples, the control portion 3000 is partially implemented in the IPG assembly 3025 and partially implemented in the remote control 3030 (at least one of patient control 3032 and physician control 3034).

FIG. 38C is a block diagram schematically representing user interface 3040, according to one example of the present disclosure. In some examples, user interface 3040 forms part or and/or is accessible via a device external to the patient and by which the therapy system may be at least partially controlled and/or monitored. The external device which hosts user interface 3040 may be a patient remote (e.g. 3032 in FIG. 38B), a physician remote (e.g. 3034 in FIG. 38B) and/or a clinician portal. In some examples, user interface 3040 comprises a user interface or other display that provides for the simultaneous display, activation, and/or operation of at least some of the various systems, assemblies, circuitry, engines, sensors, components, modules, functions, parameters, as described in association with FIGS. 1-37. In some examples, at least some portions or aspects of the user interface 3040 are provided via a graphical user interface (GUI), and may comprise a display 3044 and input 3042.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. A method, comprising:
designating a treatment period during which a patient is sleeping, a start time of the treatment period being selected from the group consisting of:
the patient turning on a therapy device,
expiration of a timer started by the patient,
a selectable, predetermined start time, and
an auto-detected initiation of sleep;
automatically initiating, at the start time, repeated delivering of stimulation, via a first stimulation element and throughout the treatment period, to an upper airway patency-related nerve to cause contraction of upper airway patency-related muscles; and
delivering upon detecting and recognizing a central sleep apnea event, via a second stimulation element and during the treatment period, stimulation to a central sleep apnea-related nerve.

2. The method of claim 1, wherein the delivering of stimulation to the upper airway patency-related nerve is performed independently of a decisional process and trigger to deliver stimulation to the different central sleep apnea-related nerve.

3. The method of claim 1, without synchronizing the stimulation of the upper airway patency-related nerve relative to a portion of a respiratory cycle.

4. The method of claim 1, synchronizing the stimulation of the upper airway patency-related nerve relative to at least an inspiratory phase of respiratory cycles throughout the treatment period.

5. The method of claim 4, comprising:
sensing respiratory information via a sensor, wherein the respiratory information includes at least the inspiratory phase, and the sensed inspiratory phase comprises at least one of:
a natural inspiratory phase; and
an artificial inspiratory phase induced by contraction of a diaphragm innervated by the stimulated central sleep apnea-related nerve.

6. The method of claim 1, comprising delivering the stimulation to the upper airway patency-related first nerve via:
synchronizing the stimulation of the upper airway patency-related nerve relative to sensed natural inspiratory phase of respiratory cycles throughout the treatment period; or
triggering the delivery of the stimulation of the upper airway patency-related nerve relative to the delivery of stimulation to the central sleep apnea-related nerve.

7. The method of claim 6, wherein the triggering the delivery of the stimulation of the upper airway patency-related nerve comprises at least one of:
delivering the stimulation of the upper airway patency-related nerve prior to delivery of the stimulation of the central sleep apnea-related nerve; and
delivering the stimulation of the upper airway patency-related nerve to extend after delivery of the stimulation of the central sleep apnea-related nerve.

8. The method of claim 1, comprising performing the delivering of stimulation to the upper airway patency-related nerve independent of detection of any obstructive sleep apnea events or detection of any central sleep apnea events.

9. The method of claim 1, comprising performing the delivering of stimulation to the upper airway patency-related nerve without regard to classification of apnea type.

10. The method of claim 9, comprising performing the delivering of stimulation to the upper airway patency-related nerve without classifying detected sleep apnea behavior as at least one of:
a mixed sleep apnea event (CSA/OSA); and
a primarily OSA event.

11. The method of claim 1, comprising delivering stimulation to the central sleep apnea-related nerve without classifying the detected sleep apnea event as at least one of:
a mixed sleep apnea event (CSA/OSA); and
a primarily CSA event.

12. The method of claim 1, comprising performing the delivering of stimulation to the central sleep apnea-related nerve simultaneous with delivering of stimulation to the upper airway patency-related nerve.

13. The method of claim 12, comprising performing the delivering of stimulation to the central sleep apnea-related nerve during at least one of:
the inspiratory phase; and
both the inspiratory phase and the expiratory phase of at least one respiratory cycle.

14. The method of claim 1, comprising:
maintaining the delivering of stimulation to the central sleep apnea-related nerve for at least one of:
at least a predetermined number of respiratory cycles; and
through the end of the treatment period.

15. The method of claim 1, wherein delivering stimulation to the central sleep apnea-related nerve comprises delivering a suprathreshold intensity level of stimulation.

16. The method of claim 1, wherein the detecting the central sleep apnea event comprises at least one of:
identifying a respiratory amplitude of zero; and
identifying the respiratory amplitude as less than a threshold.

17. The method of claim 1, wherein in the temporary absence of the inspiratory phase due to a central sleep apnea event, delivering stimulation to the upper airway patency-related nerve via a first stimulation protocol without synchronization relative to the inspiratory phase, wherein delivering stimulation via the first stimulation protocol comprises at least one of:

delivering stimulation continuously for a selected period of time; and delivering stimulation according to a cyclic pattern mimicking an intrinsic respiratory cycle.

18. The method of claim 1, comprising performing delivery of stimulation to the upper airway patency-related nerve throughout the entire treatment period.

19. The method of claim 1, comprising:

implanting, within the neck region, the first stimulation electrode/lead portion onto/relative to the upper airway patency-related nerve; and implanting, within the neck region, the second stimulation electrode/lead portion onto/relative to the central sleep apnea-related nerve.

20. The method of claim 1, wherein the treatment period is selected from the group consisting of:

the selectable, predetermined start time and a selectable, predetermined stop time; and a period of time between the auto-detected initiation of sleep and an auto-detected awake-from-sleep time.

* * * * *